US008420388B2

(12) United States Patent
Kim et al.

(10) Patent No.: US 8,420,388 B2
(45) Date of Patent: Apr. 16, 2013

(54) GENE OF PORCINE BETA CASEIN, A PROMOTER OF THE SAME AND THE USE THEREOF

(75) Inventors: Jin Hoi Kim, Yongin-si (KR); Myeong Goo Yeo, Seoul (KR); Sung-Jo Kang, Seongnam-si (KR); Jong Deok Ahn, Seoul (KR)

(73) Assignee: Cho-A Pharm. Co., Ltd., Seoul (KR)

( * ) Notice: Subject to any disclaimer, the term of this patent is extended or adjusted under 35 U.S.C. 154(b) by 0 days.

(21) Appl. No.: 12/737,318

(22) PCT Filed: Dec. 31, 2008

(86) PCT No.: PCT/KR2008/007823
§ 371 (c)(1),
(2), (4) Date: Apr. 21, 2011

(87) PCT Pub. No.: WO2010/002082
PCT Pub. Date: Jan. 7, 2010

(65) Prior Publication Data
US 2011/0209229 A1    Aug. 25, 2011

(30) Foreign Application Priority Data

Jun. 30, 2008  (KR) .................. 10-2008-0062767

(51) Int. Cl.
*C12N 15/00*     (2006.01)
*A01N 63/00*     (2006.01)
*A61K 48/00*     (2006.01)
*C07H 21/04*     (2006.01)

(52) U.S. Cl.
USPC .................. 435/320.1; 424/93.21; 536/23.5; 536/24.1; 536/24.2

(58) Field of Classification Search ............... 424/93.21; 435/320.1; 536/23.5, 24.1, 24.2
See application file for complete search history.

(56) References Cited

U.S. PATENT DOCUMENTS

| | | | |
|---|---|---|---|
| 4,873,316 A | 10/1989 | Meade | 530/412 |
| 5,304,489 A | 4/1994 | Rosen | 435/320.1 |
| 5,610,053 A | 3/1997 | Chung | 435/240.1 |
| 5,959,171 A | 9/1999 | Hyttinen et al. | 800/200 |
| 5,994,616 A | 11/1999 | Rosen | 800/7 |
| 6,136,597 A | 10/2000 | Hope et al. | 435/325 |
| 6,287,863 B1 | 9/2001 | Hodgson | 435/455 |
| 6,436,707 B1 | 8/2002 | Zambrowicz et al. | 435/455 |
| 6,548,653 B1 | 4/2003 | Young et al. | 536/23.4 |
| 7,416,886 B2 | 8/2008 | Kim | 536/24.1 |
| 2004/0133932 A1 | 7/2004 | Cooper et al. | 800/4 |
| 2005/0229261 A1 | 10/2005 | Cheng et al. | 800/14 |
| 2010/0205680 A1 | 8/2010 | Kim et al. | 435/320.1 |
| 2011/0239314 A1 | 9/2011 | Yeo et al. | 800/7 |

FOREIGN PATENT DOCUMENTS

| | | |
|---|---|---|
| EP | 2 305 814 | 4/2011 |
| KR | 10-1994-0012082 | 5/1994 |
| KR | 10-0232640 | 9/1999 |
| KR | 10-1999-0075254 | 10/1999 |
| KR | 10-2001-0081456 | 8/2001 |
| KR | 10-2004-0039168 | 5/2004 |
| KR | 10-2004-0101793 | 12/2004 |
| KR | 00141990 | * 12/2007 |
| WO | WO 01/59074 | 8/2001 |
| WO | WO 03/097818 | 11/2003 |
| WO | WO 2004/042062 | 5/2004 |

OTHER PUBLICATIONS

Sus scrofa beta casein gene, promoter region, exon 1, and partial sequence [online], [retrieved on Apr. 27, 2012]. Retrieved from the Internet:< URL http://www.ncbi.nlm.nih.gov/nucleotide/42525316?report=genbank&log$=nucltop&blast_rank=4&RID=TNCAAN5701N>, pp. 1-4.*
de Jong, entered Nov. 7, 2005, Sus scrofa genomic clone CH242-240J23, genomic survey sequence [online], 2005 [retrieved on Aug. 5, 2012]. Retrieved from the Internet:< URL: http://www.ncbi.nlm.nih.gov/nucgss/ct146582.1>, p. 1.*
NCBI [online], 2012, [retrieved on Aug. 5, 2012]. Retrieved from the Internet: <URL:http://blast.ncbi.nlm.nih.gov/Blast.cgi>, 3 pages.*
NCBI [online], 2012, [retrieved on Aug. 5, 2012]. Retrieved from the Internet: <URL:http://www.ncbi.nlm.nih.gov/nucleotide/347616012?report=genbank&log$=nucltop&blast_rank=1&RID=1Y1CR2D301N>, 5 pages.*
NCBI [online], 2012, [retrieved on Aug. 5, 2012]. Retrieved from the Internet: <URL:http://www.ncbi.nlm.nih.gov/nuccore/333785014>, 5 pages.*
NCBI [online], 2012, [retrieved on Aug. 5, 2012]. Retrieved from the Internet: <URL: http://www.ncbi.nlm.nih.gov/nuccore/NW_003300496.1?report=genbank>, 4 pages.*
NCBI [online], 2012, [retrieved on Aug. 5, 2012]. Retrieved from the Internet: <URL: http://www.ncbi.nlm.nih.gov/nuccore/206591689>, 39 pages.*
Yeo et al., submission Jul. 10, 2007 CHO-A Biotechnology Institute, CHO-A Pharmaceutical Company, 190-1, Sangdaewon 1-dong, Jungwon-gu, Seongnam, Gyeonggi-Do 462-807, Republic of Korea.*
Letter/Written Disclosure of the Information Disclosure Statement for the above referenced application mailed on Nov. 16, 2011, 2 pages.
Castro, F. and J. Juhanne (Ed)., "Selection of genes for expression in milk: the case of the human erythropoietin gene" in *Mammary gland transgenesis: therapeutic protein production* Springer-Verlag and Landes Bioscience, pp. 91-106 (1998).
English Abstract of Korean Patent Publication No. 10-2004-0101793 (Item AA), Korean Intellectual Property Office, 1 page.

(Continued)

*Primary Examiner* — Shin-Lin Chen
(74) *Attorney, Agent, or Firm* — McKenna Long & Aldridge LLP; Stephanie Seidman

(57) ABSTRACT

The present invention provides a porcine beta-casein gene, a porcine beta-casein gene promoter, an expression vector comprising the same promoter, and a method for the production of a target protein using the same expression vector. The promoter of the present invention facilitates mammary gland-specific expression of the target protein and therefore can be useful for high-concentration production of beneficial proteins in milk.

13 Claims, 4 Drawing Sheets

OTHER PUBLICATIONS

English Abstract of International Patent Publication No. WO 2003/097818 (Item AB), World Intellectual Property Organization, 1 page.

Park et al., "Production of Transggenic Pig Harboring Tissue-Type Plasminogen Activator Gene with Bovine-beta-Casein Promoter," Division of Animal Biotechnology, pp. 190 (2004). Abstract.

Written Opinion of the International Search Authority, issued Aug. 14, 2009, in connection with International Application No. PCT/KR2008/007823, 3 pages.

International Search Report, issued Aug. 14, 2009, in connection with International Application No. PCT/KR2008/007823, 3 pages.

International Preliminary Report on Patentability, issued Jan. 5, 2011, in connection with International Application No. PCT/KR2008/007823, 4 pages.

Certified English Abstract of Korean Patent Application No. 10-1994-0012082, Korean Intellectual Property Office, 2 pages.

Certified English Abstract of Korean Patent No. 10-0232640, Korean Intellectual Property Office, 2 pages.

Cho et al., "Production of transgenic pigs harboring the human erythropoietin (hEPO) gene using somatic cell nuclear transfer," J Reprod Dev 55(2):128-136 (2009).

Genbank Accession No. EU213063 [online], "Sus scrofa beta-casein (csn2) gene, complete cds," Published on Jan. 1, 2008 [retrieved on May. 17, 2011] [retrieved from the Internet:<URL:ncbi.nlm.nih.gov/nuccore/EU213063] [9 pages].

Gokana et al., "Chromatographic separation of recombinant human erythropoietin isoforms," Journal of Chromatography 791:109-118 (1997).

Johansen et al., "Increased in vitro and in vivo transgene expression levels mediated through cis-acting elements," J Gene Med 5(12):1080-1089 (2003).

Mastroyiannopoulos et al., "Woodchuck post-transcriptional element induces nuclear export of mytonic dystrophy 3' untranslated region transcripts," EMBO Report 6(5):458-463 (2005).

Mulvihill, D. and P. Fox, "Isolation and characterization of porcine beta-casein," Biochim Biophys Acta. 578(2):317-324 (1979).

Parekh et al., "N-glycosylation and in vitro enzymatic activity of human recombinant tissue plasminogen activator expressed in Chinese hamster ovary cells and a murine cell line," Biochemistry 28(19):7670-7679 (1989).

Park et al., "Recombinant human erythropoietin produced in milk of transgenic pigs," J Biotechnol(3):362-371 (2006).

Prather et. al., "In vitro development of embryos from Sinclair miniature pigs: a preliminary report," Theriogenology 43(6):1001-1007 (1995).

Roberts et al., "Cloning of the goat beta-casein-encodeing gene and expression in transgenic mice," Gene 121(2):255-262 (1992).

Schmitt-Ney et al., "Beta-casein gene promoter activity is regulated by the hormone-mediated relief of transcriptional repression and a mammary-gland-specific nuclear factor," Molecular and Cellular Biology 11(7):3745-3755 (1991).

Ziomek, C., "Commercialization of proteins produced in the mammary gland," Theriogenology 49(1):139-144 (1998).

Zufferey et al.,"Woodchuck hepatitis virus posttranscrtiptional regulatory element enhances expression of transgenes delivered by retroviral vectors," J Virol 73(4):2886-2892 (1999).

Letter/Written Disclosure of the Information Disclosure Statement for the above referenced application, mailed on Aug. 17, 2011, 2 pages.

Letter/Written Disclosure of the Supplemental Information Disclosure Statement for the above-referenced application, mailed on Dec. 7, 2012.

Alexander, L. and C. Beatte, "The sequence of porcine alpha s1-casein cDNA: evidence for protein variants generated by altered RNA splicing," Anim Genet vol. 23(3):283-288 (1992), 6 pages.

Certified English Abstract of Korean Patent No. 10-0434729 (Unexamined Korean Patent Publication No. 10-1999-0075254, Korean Patent Application No. 10-1998-0009337), Korean Intellectual Property Office, 2 pages.

Certified English Abstract of Korean Patent Publication No. 10-2001-0081456 (Korean Patent Application No. 10-2000-0006888), Korean Intellectual Property Office, 2 pages.

Written Opinion, issued Mar. 25, 2010, for International Application No. PCT/KR2009/003516, 6 pages.

International Search Report, issued Mar. 25, 2010, for International Application No. PCT/KR2009/003516, 3 pages.

International Preliminary Report on Patentability, issued Feb. 8, 2011, for International Application No. PCT/KR2009/003516, 7 pages.

Extended European Search Report, mailed Nov. 24, 2011, in connection with European Patent No. 09773696.1, 6 pages.

Office Action, issued Mar. 13, 2012 in connection with Australian Patent Application No. 2009266603, 2 pages.

* cited by examiner

SEQUENCE LISTING

<160> NUMBER OF SEQ ID NOS: 72

<210> SEQ ID NO 1
<211> LENGTH: 17660
<212> TYPE: DNA
<213> ORGANISM: Sus scrofa
<220> FEATURE:
<221> NAME/KEY: gene
<222> LOCATION: (1)..(17660)
<223> OTHER INFORMATION: gene of porcine beta casein

<400> SEQUENCE: 1

```
atcagatgtt attttatgtg gctaatctta tggaaagaat taaaatattc catctatata      60
aataatgcta tgcaatctca tggaaagaat taaaatatta catctatata aataatgcta     120
tgctacctat tcttaactaa taatttggtg gaattaacaa attttgtttt acattgttgc     180
catatctgaa tcattatata aacttcactc ttttttatc ctatttccac ccccgcccat      240
gttttggaag ttattaaaca gagtctcaaa tattatttag aaaaatgaag ttttagtaa      300 cagctctatt tctaaagagc tgcagtctcc tgaaaaaaa caatgcaaat tcacaggccc      360
tctgtttctt tgcctctaaa atatatttaa aacatcatat ggatgatatc tagggtctct     420
tctagtcctt atttttctgaa caattttttgg tccttttatt gtacttttta tccagctttt    480 cttttctttct ttctttcttt tttttttcttt ttaggcccac acttgtggca tatggaggtt    540
caggctaggg atcaaatcag agttgtagct gctgacctac accacagcca cagccacgca    600
ggatcctatc tgcatgggtg ctggtcagat ttgctaacca ctgagtcacg acaggaactc      660
ccttatcagc ttttctatta ctctattct tgagggtgtt attcacatgg tttcagctat       720
tacctttttg ctttacctat atctcatgcc tgcatatttc agattcatca tccaatattg       780
gaaaaagctt tgactgaaca aattctgctt ataacaaata gtactagaac actttgcata     840
gatcatatat tactcctcac ccagggttgt cttataaaat ttctgtggat gaaattctca      900
ctttgatata taaaaatggc aacgcttggg ttattcattg caaaagcttg gtttgcccat      960
atggcacttt gctccttact ggtcattatg ctctgaggct tacctggcca gtggcacctg    1020
atgttatctt aaatctctgg cttttcaact ctcccttggg caagtctttt tctctggtgt    1080
attgttagtg atttccttga tcaaggtttt acctactttt ctggcccaat caagtccata    1140
actgtatcta ttcatataat tcaaaattgg tgagcgatag tcataaggga atgttgtatt    1200
tattgcacaa taggtaaagc atcttgctga gaaaacacaa aggaagtatc aaatggttag    1260
ggcacacttg cttttgtatt ccttttctta gaaattatac tcttttgcct atggccttgg    1320
caaccaagag ctaacacata aaggcacagt gaacagccaa gacctttct agttataccl     1380 atgacactgg ggtcatttca tcatttcttt tcatggcttc ctcctggctc catatgaaca    1440
ctcttagaat taatattagc tgaataattt gaatacacag tagacactga gttgggtttc    1500
tgaggaatac aaaacctata tgacagtcag gaatattctc ctcccacata catctagcat    1560
gatatgaatg caaggtatct tatgaagaaa aatcattaat tatgccgata ctctacttgc    1620
ttacttcata acagcatcta tctatctata cttaagtact gaatatatct ttacaggcaa    1680
tgaatagaag aaataaagat aaaaatgagt agtctaatac aatcagccaa ttacatttat    1740
gaacatctat cactaaagag gcaaagaaac ttgaagacaa cttttatacg tgggcaacta    1800
agaaatactt tgaggcctg gctcagactc tattatagca cgttaggtga gacccctcctc   1860 ctgtctgggc tttcatcttc tttcttcctt ccatcatttg gccttcatga atattagctg    1920
```

```
acatacattg attcactata gaagatatga gaccaaactt gagaggattg atttgttttt    1980
cttttctttc tttcttcttc ttcttcttct tttttttttt tttttttttt tttttttttaa   2040
ggctgcaccc aaagcacatg gaagtttcca ggccaggggt caaatcaaag ttgcagctgt    2100
ggtctatacc acagccatag caacaccaga tctgagctgc acctgagacc aaggtctctt    2160
gtggcgatgc ggattcttaa cccactgagc aaggccaggg attgaacctg catcctcatg    2220
gacaccatgt tttgttcttg acccgctgag ccacaaaggg aattcctaaa agcaccactt    2280
taataaattt gtaccagtat catttttttc tctaaaaata ttctctaaat gttactttct    2340
gtcttaaaac ccttcaaaaa gtcctcacta tctagagaat aaaatttgca ctccttaaaa    2400
ttctttgccc actgttatgt caccccttg tctttcttct catctccatc tactcgctac     2460
tccttgcact tcataaccta aattcactat ttgatttagt tgtagtgact tgttatcat     2520
gttcaagacc atatacttcc tttcgtttta gcctacatct ctctttcttc cttaggtctg    2580
agctgtcatc acaggcttgt catgtcattt tctccattat ggcataaaat ggtaacatct    2640
atttagttag catgaaatag tgaccttcgt gtggcctgtg tatctccaat acctattaga    2700
atttccccac aagaaagctc ttgaaaacct accaagtgct aaagagacct tattgtggct    2760
accataactt ggggactggg ccagaatgtc actgtccccc agccaacgtc tgtacttatt    2820
gaacagtttc atttcctgga tggattttct ttatcagatg gtaaattatc cacttgttaa    2880
aatgctcctc agaatttctg gggatagata ataggaagaa atcatttttct aatcatgcag   2940
atttcttgga attcaaactc actattgatt ttattttcca accacacaat tagcatgtca    3000
ttaaatactg tataaaaata gccacagaag tggatgatta tccattcacc tcctccttca    3060
cttcttgtcc tccactttgg agaaaaggta agaatttcag attcaattca atgtatcctc    3120
tcatcctgat cttaaactac gttgagatat agaaagaaca tagttgctta aaaatatgta    3180
tttaatatat agggtatttg tgggtattta agatagtgct gatactattt tcagtactta    3240
gtttaaaaaa atagaagtgc ctgtaaagat ttgataaaaa tttaaatgac cgtgttgtat    3300
gaatctaaca aaatgtagta atggtgactg ctatttcctt tagtaaaaga ctagttaaca    3360
ggctgtatta aaagatacat ttcttgaatt atatgtctct caaattgatt aaacatacca    3420
cagccataaa ggcaaataca tttaatttat agcatgggta tatgaataat cattattaag    3480
aaaattttag cccacaaata gtttatagat gttgcatgtc agtcaagaaa tggagagatt    3540
tgtttgggaa catgtgctcc ttaaaatatt tataaataat attttttagaa gaagagcata   3600
tttgtcagaa ttgtttaaaa tatccaaatt ctcaatttac catttatatt atgatatttc    3660
aaaactatta aaatagattc ataaaataca gaattaaatt aaagacaaac aaaatgttta    3720
ctttgtgaaa aaaaaaaaat cctagggggga acagagttta tctgggaaca aaaaagaagg   3780
aaaacatgat ctgaaataaa gaatagttta aaattcatgg agttccagtt gtggctcagt    3840
ggtaatgaac cctactagta tccatgagga catgggtttg atccctggac ctgctcagtg    3900
ggttaaggat ccagcattgc tgtggctgtg gcatgggcca gcagctacag cttcaattca    3960
atccctagcc taggaatttc aatatgccaa aaaaaaaaaa aaaaaaggc aataataaaa      4020
atcctggctt aaaaatttat aaataaaatt ataattataa aataaagaac atgtaataat    4080
atcttcccta cttgtaaaga attctaataa agtactatat tcttttttc agtctctaca     4140
gtaaaaaata tttggaaatg tttgagaatt tctgcataaa gtaaaatcaa taaggaataa    4200
gacagcaccc atgagaaaaa tctagggcga aagtcttaa tttagtaaaa atcttggatt     4260
gaagattgcg tgtcaaggga tattggtggc acaaacatta ttttttttac aaaacttttta   4320
```

```
gaaatgcagt aaaatctacc atttagtaca ttttggtcaa agtattaac atattttatg    4380
ctatgcagcc aggagaagta gcctagagtg gggaagtagc ctggagtggg gaagtagcct    4440
ggagtgggga ggtagcctgg agtgggaga tagcctggag tggtaagcag cctagagtgg    4500
ggattgggca agtgaacctg acctttggt aaatcatcaa gagacaagtg cacacatgtt    4560
cacagagatg aaagaaggag agtgtataat ctccacaatt atgtggcaca aggagaaga    4620
gatgctgtta ggtatggggg attaggactg tgaggtggat atatatggag aagaaacaaa    4680
ccattccgcc caagaaaaca tctggataag tggagcaagt aaacgaaata ctaaaatgaa    4740
aagctcagtc ttatggaaat aaaaagctat gtataagcca attatccata taaatcattt    4800
agttcaataa agctaaaata aaatatgacc ttctttgtat gcattttatc tgataacttt    4860
cctctctgta gaactgaggc tccaataggg ctgagacctt actattttgt tcactgctaa    4920
cattccagca cataagcaaa gtctggcaat aaaaagtgct aaataataag cactgagaaa    4980
ctgctgtaca gcacagagaa ctctatccaa tcacttgtga taaaacatga tagaagataa    5040
tatgagaaaa agaatgttta catatgtatg actgggtcac tttgctgtag agcagaaatc    5100
gacagaacat tgtaaatcaa ctgtacttca attttaaaaa attttaaaag gtgccaaata    5160
aatattttg aatctattaa ttaagctttc tgtcaatatt tgtagcttct gtatttcaaa    5220
agaaaaaact aatatgtact gtgaaatgag atgaaaaga ttgaagtagg ataaggctgt    5280
tagtggaaaa aatctgaatg gctggcaatg aaataggaac ttgacatgta agattaagga    5340
gtcatagtag atgttgaccc tggtcatatg acaaaatttc tatcagacat ttttattaca    5400
cctttggttt cttttagagg aaataaaata agaaatatat tagattgacc agtcatatac    5460
attttttccc tcatttcccc attcacagga cttgatcgcc atgaagctcc tcatccttgc    5520
ctgcttcgtg gctcttgccc ttgcaagagc ggtaagtaca gaaaaaaaat ctctgaataa    5580
ataaggaata gtactacctg cctatgggta gaaaatggta ttaccaacac tgtaaaggta    5640
taaataatgc agaagagcag gtttgttttt gtttgtttat tttttcactt ctaagaaaat    5700
cccttgcatt tacccaccat ctcaacaata tccactgggg ccacacatct ggatcaaatg    5760
cttttctgtag tattgtgcca ccagtgccta aggtaatcaa gcaaaccaat aagcaacaga    5820
taaacaagaa gaaacacata tgagaacaat aaaagagta atattacaca aatacacttc    5880
catcttcttc cagtgatgaa atatatgatc tctagggcac ccagttaaat cctacctgtg    5940
tctattgaac agagaatgat actccagaag atggggtatc agacaataat cacaaacata    6000
ttcataatca taatgaaagt attcaataca aatgaaaata actttttttt ctgttatcca    6060
taaaaaactc ctcattaagg aaaaataaaa atataccagt aaaaagttaa tacatttaaa    6120
taatgtaaaa gcaattacaa gtctctcaaa agacatagaa catattttt cagtttgtga    6180
aatagatagc tctgcataag gaaggtaaaa ttcagatagg aaaaatgttt aataatgagt    6240
caactatggg gactaaaatg ctggtttttc tttttttct ctatagaagg aagaactcaa    6300
tgcatctggt gaggtaagat atttttattc agagaaaaat tcccaagcat aaaatagtaa    6360
aactttctga tgatctagca gatttagctg gaggttgaat ttcaactttt cctttctttt    6420
ttcctttttca gactgtggaa agcctttcaa gcagtgaggt aagccaatgt ttattcatag    6480
gtaatttccc aaatttagaa ctattaaaaa aactgcacta tctttctttt agtgtgaaca    6540
cgaacatgca ttgatgaagc tatcatatct atattctgac acttaagttc taatgtaaat    6600
ttccattgta tatattttaaa gagagaatac atgtccggag gatttaacgt tctagccatt    6660
tctgagttga ctggctactt gaaattgtgg cactgtgctc cgcttcttct tcttttttt    6720
```

```
aatgaactgt acagtctttt tttctatctt gatctctctc tatattaacc tcattcactg   6780
ttttgacatt tattgataca tttatgtatc agactttaac tagagctgcg gtacaaactg   6840
gaaagaggga agcccataag aaagatctcg cagtgtagtc aggggcgga tgtacaaatg    6900 gacacatttt gtcattataa tagcataata gcagtctagt aaataagagg tagttagact   6960
tagtctagtc ctaaatctgc ccagggtgtc agtcaggtag atattaaccc tcacatcact   7020
ctttgagtct gttatcacct gttagtgaaa tggtacatca ctaaactttg actcttcaca   7080
aaggttatga gatcctagag ggaggatatg tatttcttat aattcataac aagcggacta   7140
agaatgagta acaaaggtat cagtgattat atatatacac acacatattt ttgtcttttt   7200
gccttttcta gggctgttcc tgcagcatat ggaggttccc aggttagggg tctaatcaga   7260
gctgtagccg ctggcctaca ccagagccac agcaatgtgg gagtgggacc tgagccgcat   7320
ctgcgaccta caccacaact catggcaacg ccaaatcctt aacccactga gcaaggccag   7380
gaatcgaacc cacaaactca tggttcctag tcggatttgt taaccactgg gccacgacag   7440
gaactctgat tactgtattt tcaatgactg ttattctttt caaatcagat gggttattag   7500
agatcctttg tcattgtaag aagggtaata gagagaaatt agtatctgtt ataggcctct   7560
gttgttacta tgctcactca ttttctttcc ttttatgact gcatcatctg ttcttctttt   7620
atacaataga tttattcaga atagtgtaac ataaatttcc agcaattaaa ataatattat   7680
caaacaaggt gtccacatta acctataaaa tgtcatttgc tgacttatat tgacaaataa   7740
gaattgttct ttaaaactca atcttatttt tattttccta aaggaatcta ttactcacat   7800
cagcaaggta aagacttcat ccttaaatac gcctatttc aaaacttcct gtttacttgt   7860
tacaaatagc aacatttatt ttggtgtgat ctgttttcta ggagaaaatt gagaagctta   7920
agcgggagga acaacaacaa acagaggtaa tttgttcatg atgagcatat tttgaaaatt   7980
attattaaac atgatatatg caaaatgttt atatgttcac tcaaaacat ggtattaata    8040 taaatcagtg taagaaatta aactatgaca aagtgaaaag attttaaaga catagacaca   8100
tttaaataca taatcaactt ccagagtaaa gaataagtac ctgtgaataa ctattgattt   8160
attcatttta ccaacagtat acctgttttc agtaagtgca cttaatggga acatttccgg   8220
ttccgggctg tgatcccctt gatgaaagag tagggaggtg gtgcaccacg aatcctgatt   8280
ggatcctata tcagctgtat aaccctggtc ccaagtttct ctgtacctca atttcttctt   8340
ctgtaaaatt gagaaaattc ataagccaat agggtggatg agctggcaca cagtgactat   8400
ccaatgattt tacattaaca ttctgtagct tttatactca tttatgaatg tgtgaaggtc   8460
ttaaaaaaat ttccattaca cagttgagaa aagtaagata cagaacaatt gagtacacaa   8520
ttgtgtgaca acttgcatag ttattaataa gcagggcttg cttaaaaaca aggatttgag   8580
gatgaaataa aattctttaa ttaaattact cttgtggtaa catatttatc caatcatgat   8640
atttaagctt tcctgtttta ccaatgaagt tggattattt ggtacttacc ccaaatattt   8700
tctaaatcaa aatgaattta caaatttatg cctctttaaa aactcaagat taccacttta   8760
taccaaggga agtagtgctg gaagtttgcc attaagtacc tccttgaatt aaaaacacaa   8820
attaagactt aaacaatata aatcttggag ttatccaagc cttttgggg aagaactctt    8880 ccttcattat atgaaaacaa tttggtctat tatcaacaca ttgttgtaaa gtctgtaccc   8940
tctgaagacc aaagtaagta gctacagctc tgcaggcagc tcaggaaaag gtgaaacaaa   9000
tcttgacatc tccaaacact gatttccctt ggctctgcgc attgcctagg aaggaagggg   9060
ttagggagca gtccctccat gagcatttta cccagttatc ctcacatggt atgactccta   9120
```

| | |
|---|---|
| aaccaaaaga agtgaacaat tgttctctct ttcacttaat tatgactgtt caaaaaaga | 9180 |
| ggccgctaat tcatcatgaa tgacggttgt agctgcatta cggactcaac gattcttttt | 9240 |
| ccttctttcc agaatgaacg ccagaataaa atccaccagt ttccccagcc tcagcctcta | 9300 |
| gcccatcctt acaccgagcc catcccttac cccatccttc cacaaaacat cctgcctctt | 9360 |
| gcccaggtcc ctgtggtggt gcctcttctt catcctgaag taatgaaaga ttccaaagct | 9420 |
| aaggagacca ttgttcccaa gcgtaaagga atgcccttcc ctaaatctcc agcagagcct | 9480 |
| tttgtggaag gccagagcct aactctcacc gattttgaag tcctttctct gcctctgctc | 9540 |
| cagtctctga tgcaccagat tccccagcct gttcctcaga cccccatgtt tgctcctcag | 9600 |
| cccctgctgt ccctgcctca ggccaaagtc ctgcctgttc ccagcaagt ggtgcccttc | 9660 |
| ccccagagag atatgccctt ccaggccctt ctgctctacc aggatcctct acttggccct | 9720 |
| ctccaagggt tctaccctgt gcctcaacca gttgccccag tttacaaccc tgtaagtcca | 9780 |
| agtttattca ctgtgctgtt tcacttatgg tgtttagttg ctgttagagt aattaagcaa | 9840 |
| gaactctaga ataaaagaga caatgaataa taagtggttc caaaatgcac atagtttaga | 9900 |
| tagtgattct caacatttgc tacaaataga ataaccaata actgggagat ttcctcccaa | 9960 |
| atctcaaagt ccaggattac ccacaaagat tcgacataat tgtacttacc tctatatgta | 10020 |
| ggggaaattg aatattggga agagataatt tcagggatta tgatttaatt ggtctgttga | 10080 |
| gaattgagat aaagagagag gatttaaggt atactaaagc cagaattaaa tgtaacaatc | 10140 |
| tcatgtggct tggaataaca aacctaagaa ggtttgttat tatctgcaat tttgaagttt | 10200 |
| tccttatgtg caattatttc cccacatgcc tcatttcaca tcttgttttg atatatgaac | 10260 |
| atttgagggc aagatactga gatgcctatt tcaatactca tggaatactc agggaaattg | 10320 |
| ttcttgccaa aagatgaatt gtatatttat tcgcttttt attttttaat ttttaaggtc | 10380 |
| taagaggatt tcaaagttaa tgccctctcc tcacttttgg taagctttaa gagtttgaaa | 10440 |
| atcagattaa tcattttat agttagtatc tttctgcact tcattctcct ggataagcct | 10500 |
| aaaataaagg caaattccat caatatggca acctaattat taattatcaa tttattctca | 10560 |
| ttgattgatt atttactgaa tcttttaatt agctatgaat cttttctatt tcaaatcatt | 10620 |
| caaaattgta tttatgtact gttggcagat ttgattggtt ttctttcagt tgcctataca | 10680 |
| cttacacttg atttcatca ttgttatgga aaactaaaaa taatttattt tacttttatg | 10740 |
| taaatatagt agagctattt taaagaccaa ctgcattcac atttcttact taggctttat | 10800 |
| gaacttcaag tatttttaat ctcatttaaa atgtataaat tttctcttaa ttcatgagtc | 10860 |
| aaaatgcagt tcactagtcc agatataaag cttaaaaaag gaagtcaata cagttttgag | 10920 |
| attcttaaaa cacacaccct tttgtgatca tgatatagta aacattttaa taaaacaatt | 10980 |
| ctaggtgaga tgatatttt tcctagagga acttttatat gcctccaaga tagggcacag | 11040 |
| catgaaacat ttgtaataaa atttctctta tgaattagtc atatcagaat tacagagggg | 11100 |
| aagagattag ttttataaca taattaattc tatatttgtt ctctattccg cagaattgac | 11160 |
| tgtgactgga aatgtgacaa cttttcaatc tttgcatcat gctaccaaat aattttttaaa | 11220 |
| tgagtctaca tgaaaaaaat gaaactttat tctcttattt attttatgct ttatatggcc | 11280 |
| ttcatcttaa tttgaatttg actcagaaat tctctatttt caaaatttta attcaactaa | 11340 |
| tagcacagaa tttcaatttt gagttggaaa taccatgaat atttcaaaaa tatgtataaa | 11400 |
| aataatttat ggaattataa tttcctaacc agtcatttca ataaattaat ccttaggcat | 11460 |
| atttaagttt cctgttttta ttataatttt ccaaacctaa ctggcctctt tattagttaa | 11520 |

```
cttaaagtta ttattaatgt taaaaatagc cacggaaaaa ttgaaattga gtagaatgct   11580
ttgacttgag tactaaatta tatcaaaaat ggaggaaaag gcagggtgat ctaatgctga   11640
atatactcta gaaagtcttg gtttatacct cttatctcag ctgaactatt atacttgtgc   11700 cttttcactct caaaagtatc tgcattggat gttaaatttt atgatcctcc tagataagaa   11760
ggcttccaat gtaaaatctg aatcacggct ctgtaacatg gtggctaaat ggtgctgtat   11820
aagttaggct ttcaaagatt cagttttgc atctataaca cagtcagttg aaagggtttt    11880
attgaagttt taatgtgaat agcaccccac acagtgcagg atgggtgtcc gtgtggctcc   11940
acattcctca cttacactag agcagccagt gccagtgtca caatgagaat gagctgaagg   12000
atgttgtttt agccactaat gcccaagaga gtagactat gtgaagctct gatatccctt    12060
gtctctgtct gtggagtaat tttttcattg caatgaatta tctgtctacc aactatcacc   12120
gaagtatcgg ctgcctctat acactgacgc caaatagaaa tgtggaaacc ggcaaaagta   12180
gctttaattg ccaggcagag ggtacacagc aggctagtgc ttcgaggact gtgtgcctct   12240
tggaggagtg gtgaggactc ttactcttac tcttcaagga gccgggcatg atcagccctt   12300
ggatattttc ctaactgttt ggtgatgagg taattgggag tcagcatcat caaccttctg   12360
tttccaactg gtctggggtc tacatgtttg tgggcagcat gcagttgact tcttccgcct   12420
ggtaggggtt tgagcacctg caaaaccgtt ccaaggacta ggctcagcat attatctata   12480
gtccatgagg aagaaccata agtccttgac attgctgagt ggctaaacta ttattactct   12540
gtcttgcttg actgtattcc tttttctctg tattttctca cttctctgat caaactgatt   12600
ctttgactaa agttttctcta tagacaaaaa tgcaggcaga ggacaagagt gtggatccac   12660
tgtgggaagg cttcacaggg tcctgcttgg ttacacaact cctacatttg taaacttgat   12720
tccctcccct tgtgtttaca caaggacttg tttctagcag taatttcatc tttcctgcat   12780
cctcagtgtt ttccttacct caggatcaag tgcaagccat acttaggcta taatatctcc   12840
catctttaaa gaaaaaattc catccttggc agtactttag actgctctat ggtaaccatc   12900
agaaaggaag tgtccaaact actgtgtcta ttgtttcaca tggtattctc tcatcaacct   12960
gttcccattg agctttaccc ctatggtaac cacttttttc aagattacca acaacattca   13020
ttttaccaat ctatgtttat tttacccaaa ctatcagtgc tatttggtcc agttgatcat   13080
tccttttttt tttttttttt tttgaaatat cgcaaatttt atttgaaatc ctaagcctga   13140
taagcccttg atttccctct taactcacca gttatttctt tgcatcgtct cttctggcat   13200
tttctccttt tccaaacatg caatgtgtgg aataccctag ggattagcct tactatgatt   13260
gatgttgttt gattccatga ctttaagtcc attcatgggc ttgaagcttc cacatgtatg   13320
tcctcaaact tattttttcc tgaactccaa attcaagtgc tcaactgcat tcttctccac   13380
atcggagtat ctaattaata tctcaaacct gacatggcca gcagaacttt tgtctgaat    13440 ccagtcccca aattgtccaa aatttaattg ggcatatttc aataacaaag gcaactaata   13500
taatagtgca caagcaatat ctttgaatgg gcacttcacc aaagaggtta ttttaattgt   13560 caataaaatat atgaaaagat gttcaatacc attatttctc tggaaaatgc aagttaaaaa   13620
taccagatat catgacacaa cctccagaat agctgaatga gaagaattgg taaaaccaag   13680
tatttacaaa aataagcaaa ctgaataaat gctaggtaat gttaaaataa atataaaatg   13740
gttcaagcaa ctcggaaagt attatgagtc tttgtcaaaa ataaacatct gcttatatta   13800
taactaacat ttcttctctt aggtatacaa ccaaaaggaa accataatat gctttcatat   13860
gtattctaaa aacatttacc caatactcct aacaatgcta atacctaaa ctaaaatcaa    13920
```

```
cataaatgtg aattaacatt tacgttattt tgtataaatt tgtattttgt ataaatgtat    13980
tttgtataaa taagtcatgg tctaaagtgg aatgggatat catactgcag ttgaaatgaa    14040
tgagttactg ccacaaaaaa acaagggtga attttatata aataacattg aatgacagta    14100
atcaggccaa aatataatgg aatatgtaat ccaataagtg gaatttatta gaatctaatg    14160
atcgattaaa ttcttgtgtg ataagctaga ctattggtta tctgagggaa ggtacaactt    14220
gacagaaaat gtgagaaagt gctggggaac tagcgatatt cttteeetta gectggaagt    14280 aagtatctgt ggtgattcat tgtgatgtgt gcattcagta tattgcctgt cttcttcctt    14340
ttccctgtgg ttgggacctc atcaatgcag actcacctct ttgctgttgg acttgaatgg    14400
gattgtgtac tatagcacag gaccgggttt cctcagaaac tgtaatagtt ggttaatgct    14460
actgttatat gcatagtttt agcccccact gaggtgaaaa tttcagaatg agaagcagga    14520
gatgagagag aacttgcaga tgaattctcc tttttttttt tttttttttt tttgctgtat    14580
attacagcga ggtggtaatc acacaagacc taacattttt gatagttaaa ggagacccat    14640
acagtttaca ctaacagaac agctttatta caggcagagg acagagtaca acaacaggag    14700
aagggtatgc attgaaagat gaaagaggta ctgagatctc aagagcaaac ttcatttatc    14760
ctcctactgc ttggtagcac aagacatgtg ttatcttcag ttcttaggcc actaacagag    14820
ggtgtgcaaa gcacctcaat actaggaagc tcaaaatgac ttgtgagatc tcttacaata    14880
agctcatcaa gcaggcatat tttagctata taatgagtca acaattgaat gccaaacccc    14940
attttacttc accactccta gattctccta aatctggtgt aaaccacatc cacttattac    15000
taaacaatgt ttaccagcca gtacatcctg cccatagcaa ctcacagaca tacagttaca    15060
aataacattt accaagatcc aggtgccagc agatcctgtg tccggtgaag gctccctctt    15120
ggcctgcagg tgcctgcctt tctgctgtat cctcacaagg cagaaagata gacaagctct    15180
ctcctagctt ttcttagagg ggcactaatc ccactcatag atatcccact cacatgacct    15240
atttgcctcc aaagatgcca cctccaagtg catcacatgg gggagttagg gcttcaacat    15300
atgaattcgg gagggcatgc aaaatctaat ctatagtgat taatatgaca tgaatccata    15360
aaatggatag ttcttgtgaa agttaggaca ataggaaccc aactattgaa agtggaatat    15420
atgggaaggt atggaaaatt tacagaaccg cctgctccca agtgctcctg aaggtcttac    15480 tgtaaggggga gcatggagaa aaagagaagg aattgggtgt tcaggcaaag agaagaaaat    15540
ttattagaag gaaaaggag aggctgactg acctttgaga agagtcagcc ccccgccct    15600 tctagcaggg ccttcttata ctctgcagag gggaaattga ttcctgaagc ggggaaggt    15660 tagtttatag tttatctttc acctgcaggt ggactctggt ggtcacatcg tcatgagaaa    15720
gtcagaggta tctcacggta gggtgcactc ataatcttga gaaagctgga ggtgtgtggt    15780 ccccctggt cttgtagtct tgggaaaata ggcaccagtg gcaaaacag gatgtcgctt    15840 gaacaagatg gtcagtctca tgggtcagca tgatgagcca ttttaacaat gagccccatg    15900 taaccccctaa cacttactgt gtatttgtca tgatggaatc atgatttctt tgtttactgt    15960
agctaattat taccctaatg tcctacttct cactttcact tcactgtaac tgggattcaa    16020
ccttgattgg actggaagta gaaagtcctt tacttaatga cttaaagtac actatagtac    16080
atagactagt gttagagggg ttgggtctgg ccaataaaga gaaggagact gtgtatttta    16140
tatttaaaaa acactagacc aatatttaaa aataggagat cttacacaca atccacattt    16200
ctagttcacc tagaagtccc caaatttggt tacatttgac ctgtgtattc ctgcacagca    16260
acaatgcatt ggaaggggca gccaatgagg aatgcacata ttcttcagtt cactgtcagc    16320
```

```
actgttttt    cacaactgta  ttttttttctg  cttctgttat  ttgtaagact  ctagaaggca   16380
gtttgacaat   cataattgaa  agagaaatat   ttaaacatcc  ataaatagat  atgcttagtt   16440
ctaatggccc   tgcacttccc  tgtgtctaca   aaggataaat  tattctcctt  taaactttc    16500
cttgaagggt   aaacttttat  gaaattcttt   tgtgctaaac  aattgactga  gaactctggt   16560
gagaggtgca   aagtaattga  aattgcattt   ccaacctcag  ggaaaatgga  aggagactag   16620
tgtcaccaaa   ccaagtgaca  actggtaaaa   agcgttata   ggcaaaaaat  acatgtttag   16680
gtgttatgca   tatatgtgca  tatcaattat   atatataatc  gataagagac  agaactgcta   16740
actaaatagg   tcgtttaggt  tgtggtacaa   gagaccttgc  cacctgtatt  ttatgacctg   16800
gtggaaagaa   gtttcttaaa  gagtcacagc   agatagggtt  tgttgggggac cctggaataa   16860
actctggaaa   gtaaattcca  gcagggtttt   gagggtatta  atgcaagcga  ctattgtcat   16920
tttgagaaat   aactcttcat  tggagttcgg   gaggacactg  agtattgtgt  tactgtatgc   16980
catggtctaa   cctattaaat  gtttattatc   taatctacct  aattataaaa  gtaagtgtat   17040
aataatcaaa   taatcaaatg  agtttggctc   aaacaggttc  tggtgacata  aataaacagc   17100
ttagccatgt   ttttcaaatt  cccagtgcac   ccgcaactgt  cataccactg  ttcttctctg   17160
cagccacacc   tatgttctca  tggagaatat   cctatagaca  ggtgacttca  aatgaaagat   17220
cctagaccca   gctataacc   tgtcagcatc   agctaggcat  gaagatttac  cattttgttc   17280
attgaattgt   ggttgaaagt  gtaataaaaa   tttagtgaaa  ataaaatgtt  acaggcataa   17340
agactgttaa   caggattgtg  caaattctgc   tgaatgaat   aatgacaaaa  ataggagtt    17400
gtgccttaaa   atgtaattta  ttgaaaagaa   ggaagaaaaa  tctcagtcac  tgcacacaat   17460
tatttgaaat   gatggcactt  acaggagaag   caattcaaag  gcttttttaaa caaaatttcc   17520
atattgaaat   ttagtaaaga  cttttaattc   cctctgattc  agtggtcttc  ctactggcat   17580
gatacaactg   aaatttagac  actaaactgt   taggacaact  ttgccaaagg  aaaaggatta   17640
tatgctatct   aatatagagt                                                    17660
```

<210> SEQ ID NO 2
<211> LENGTH: 5480
<212> TYPE: DNA
<213> ORGANISM: Sus scrofa
<220> FEATURE:
<221> NAME/KEY: promoter
<222> LOCATION: (1)..(5480)
<223> OTHER INFORMATION: promoter of porcine beta casein

<400> SEQUENCE: 2

```
atcagatgtt   attttatgtg  gctaatctta   tggaaagaat  taaaatattc  catctatata    60
aataatgcta   tgcaatctca  tggaaagaat   taaaatatta  catctatata  aataatgcta   120
tgctacctat   tcttaactaa  taatttggtg   gaattaacaa  attttgtttt  acattgttgc   180
catatctgaa   tcattatata  aacttcactc   ttttttttatc ctatttccac  ccccgcccat   240
gttttggaag   ttattaaaca  gagtctcaaa   tattatttag  aaaaatgaag  ttttttagtaa  300
cagctctatt   tctaaagagc  tgcagtctcc   tgaaaaaaaa  caatgcaaat  tcacaggccc   360
tctgtttctt   tgcctctaaa  atatatttaa   aacatcatat  ggatgatatc  tagggtctct   420
tctagtcctt   attttctgaa  caattttttgg  tcctttttatt gtactttta   tccagctttt   480
ctttctttct   ttctttcttt  ttttttcttt   ttaggcccac  acttgtggca  tatggaggtt   540
caggctaggg   atcaaatcag  agttgtagct   gctgacctac  accacagcca  cagccacgca   600
ggatcctatc   tgcatgggtg  ctggtcagat   ttgctaacca  ctgagtcacg  acaggaactc   660
```

```
ccttatcagc ttttctatta ctctatttct tgagggtgtt attcacatgg tttcagctat    720 taccttttg cttacctat atctcatgcc tgcatatttc agattcatca tccaatattg      780
gaaaaagctt tgactgaaca aattctgctt ataacaaata gtactagaac actttgcata    840
gatcatatat tactcctcac ccagggttgt cttataaaat ttctgtggat gaaattctca    900
ctttgatata taaaaatggc aacgcttggg ttattcattg caaaagcttg gtttgcccat    960
atggcacttt gctccttact ggtcattatg ctctgaggct tacctggcca gtggcacctg   1020
atgttatctt aaatctctgg cttttcaact ctcccttggg caagtctttt tctctggtgt   1080
attgttagtg atttccttga tcaaggtttt acctactttt ctggcccaat caagtccata   1140
actgtatcta ttcatataat tcaaaattgg tgagcgatag tcataaggga atgttgtatt   1200
tattgcacaa taggtaaagc atcttgctga gaaaacacaa aggaagtatc aaatggttag   1260
ggcacacttg cttttgtatt ccttttctta gaaattatac tcttttgcct atggccttgg   1320
caaccaagag ctaacacata aaggcacagt gaacagccaa gacctttct agttataacct  1380 atgacactgg ggtcatttca tcatttcttt tcatggcttc ctcctggctc catatgaaca   1440
ctcttagaat taatattagc tgaataattt gaatacacag tagacactga gttgggtttc   1500
tgaggaatac aaaacctata tgacagtcag gaatattctc ctcccacata catctagcat   1560
gatatgaatg caaggtatct tatgaagaaa aatcattaat tatgccgata ctctacttgc   1620
ttacttcata acagcatcta tctatctata cttaagtact gaatatatct ttacaggcaa   1680
tgaatagaag aaataaagat aaaaatgagt agtctaatac aatcagccaa ttacatttat   1740
gaacatctat cactaaagag gcaaagaaac ttgaagacaa cttttatacg tgggcaacta   1800
agaaatactt ttgaggcctg gctcagactc tattatagca cgttaggtga gaccctcctc   1860
ctgtctgggc tttcatcttc tttcttcctt ccatcatttg gccttcatga atattagctg   1920
acatacattg attcactata gaagatatga gaccaaactt gagaggattg atttgttttt   1980
cttttctttc tttcttcttc ttcttcttct tttttttttt tttttttttt ttttttttaa   2040
ggctgcaccc aaagcacatg gaagtttcca ggccaggggt caaatcaaag ttgcagctgt   2100
ggtctatacc acagccatag caacaccaga tctgagctgc acctgagacc aaggtctctt   2160
gtggcgatgc ggattcttaa cccactgagc aaggccaggg attgaacctg catcctcatg   2220
gacaccatgt tttgttcttg acccgctgag ccacaaaggg aattcctaaa agcaccactt   2280
taataaattt gtaccagtat cattttttc tctaaaaata ttctctaaat gttactttct    2340
gtcttaaaac ccttcaaaaa gtcctcacta tctagagaat aaaatttgca ctccttaaaa   2400
ttctttgccc actgttatgt cacccctttg tctttcttct catctccatc tactcgctac   2460
tccttgcact tcataaccta aattcactat ttgatttagt tgtagtgact tgttatcat    2520 gttcaagacc atatacttcc tttcgtttta gcctacatct ctctttcttc cttaggtctg   2580
agctgtcatc acaggcttgt catgtcattt tctccattat ggcataaaat ggtaacatct   2640
atttagttag catgaaatag tgaccttcgt gtggcctgtg tatctccaat acctattaga   2700
atttccccac aagaaagctc ttgaaaacct accaagtgct aaagagacct tattgtggct   2760
accataactt ggggactggg ccagaatgtc actgtccccc agccaacgtc tgtacttatt   2820
gaacagtttc atttcctgga tggattttct ttatcgagatg gtaaattatc cacttgttaa   2880
aatgctcctc agaatttctg gggatagata ataggaagaa atcattttct aatcatgcag   2940
atttcttgga attcaaactc actattgatt ttattttcca accacacaat tagcatgtca   3000
ttaaatactg tataaaaata gccacagaag tggatgatta tccattcacc tcctccttca   3060
```

```
cttcttgtcc tccactttgg agaaaggta agaatttcag attcaattca atgtatcctc   3120
tcatcctgat cttaaactac gttgagatat agaaagaaca tagttgctta aaatatgta    3180 tttaatatat agggtatttg tgggtattta agatagtgct gatactattt tcagtactta   3240
gtttaaaaaa atagaagtgc ctgtaaagat ttgataaaaa tttaaatgac cgtgttgtat   3300
gaatctaaca aaatgtagta atggtgactg ctatttcctt tagtaaaaga ctagttaaca   3360
ggctgtatta aagatacat ttcttgaatt atatgtctct caaattgatt aaacatacca    3420
cagccataaa ggcaaataca tttaatttat agcatgggta tatgaataat cattattaag   3480
aaaattttag cccacaaata gtttatagat gttgcatgtc agtcaagaaa tggagagatt   3540
tgtttgggaa catgtgctcc ttaaaatatt tataaataat attttagaa gaagagcata    3600 tttgtcagaa ttgtttaaaa tatccaaatt ctcaatttac catttatatt atgatatttc   3660
aaaactatta aatagattc ataaaataca gaattaaatt aaagacaaac aaaatgttta    3720 cttttgtgaaa aaaaaaaat cctaggggga acagagtttta tctgggaaca aaaagaagg   3780 aaaacatgat ctgaaataaa gaatagtttta aaattcatgg agttccagtt gtggctcagt  3840
ggtaatgaac cctactagta tccatgagga catgggtttg atccctggac ctgctcagtg   3900
ggttaaggat ccagcattgc tgtggctgtg gcatgggcca gcagctacag cttcaattca   3960
atccctagcc taggaatttc aatatgccaa aaaaaaaaa aaaaaaggc aataataaaa     4020 atcctggctt aaaaatttat aaataaaatt ataattataa aataaagaac atgtaataat   4080
atcttcccta cttgtaaaga attctaataa agtactatat tcttttttc agtctctaca    4140 gtaaaaaata tttggaaatg tttgagaatt tctgcataaa gtaaaatcaa taaggaataa   4200
gacagcaccc atgagaaaaa tctagggcga aagtcttaa tttagtaaaa atcttggatt    4260
gaagattgcg tgtcaaggga tattggtggc acaaacatta ttttttttac aaaacttta    4320 gaaatgcagt aaaatctacc atttagtaca ttttggtcaa agtattaac atattttatg    4380 ctatgcagcc aggagaagta gcctagagtg gggaagtagc ctggagtggg gaagtagcct   4440
ggagtgggga ggtagcctgg agtggggaga tagcctggag tggtaagcag cctagagtgg   4500
ggattgggca agtgaacctg acctttttggt aaatcatcaa gagacaagtg cacacatgtt  4560
cacagagatg aaagaaggag agtgtataat ctccacaatt atgtggcaca aggagaaga   4620 gatgctgtta ggtatggggg attaggactg tgaggtggta atatatggag aagaaacaaa  4680
ccattccgcc caagaaaaca tctggataag tggagcaagt aaacgaaata ctaaaatgaa   4740
aagctcagtc ttatggaaat aaaaagctat gtataagcca attatccata taaatcattt   4800
agttcaataa agctaaaata aaatatgacc ttctttgtat gcattttatc tgataacttt   4860
cctctctgta gaactgaggc tccaataggg ctgagacctt actattttgt tcactgctaa   4920
cattccagca cataagcaaa gtctggcaat aaaaagtgct aaataataag cactgagaaa   4980
ctgctgtaca gcacagagaa ctctatccaa tcacttgtga taaaacatga tagaagataa   5040
tatgagaaaa agaatgttta catatgtatg actgggtcac tttgctgtag agcagaaatc   5100
gacagaacat tgtaaatcaa ctgtacttca attttaaaaa attttaaaag gtgccaaata   5160 aatattttg aatctattaa ttaagctttc tgtcaatatt tgtagcttct gtatttcaaa    5220
agaaaaaact aatatgtact gtgaaatgag atgaaaagaa ttgaagtagg ataaggctgt   5280
tagtggaaaa aatctgaatg gctggcaatg aaataggaac ttgacatgta agattaagga   5340
gtcatagtag atgttgaccc tggtcatatg acaaaatttc tatcagacat ttttattaca   5400
cctttggttt cttttagagg aaataaaata agaaatatat tagattgacc agtcatatac   5460
```

```
atttttttccc tcatttccccc                                         5480
```

<210> SEQ ID NO 3
<211> LENGTH: 5299
<212> TYPE: DNA
<213> ORGANISM: Sus scrofa
<220> FEATURE:
<221> NAME/KEY: promoter
<222> LOCATION: (1)..(5299)
<223> OTHER INFORMATION: Pig beta casein promoter 5.3kb

<400> SEQUENCE: 3

```
gctatgcaat ctcatggaaa gaattaaaat attacatcta tataaataat gctatgctac    60
ctattcttaa ctaataattt ggtggaatta acaaattttg ttttacattg ttgccatatc   120
tgaatcatta tataaacttc actctttttt tatcctattt ccaccccgc ccatgttttg    180
gaagttatta aacagagtct caaatattat ttagaaaaat gaagttttta gtaacagctc   240
tatttctaaa gagctgcagt ctcctgaaaa aaacaatgc aaattcacag gccctctgtt    300
tctttgcctc taaaatatat ttaaaacatc atatggatga tatctagggt ctcttctagt   360
ccttattttc tgaacaattt ttggtccttt tattgtactt tttatccagc ttttcttttct   420
ttcttctttt ctttttttt cttttttaggc ccacacttgt ggcatatgga ggttcaggct   480
agggatcaaa tcagagttgt agctgctgac ctacaccaca gccacagcca cgcaggatcc   540
tatctgcatg ggtgctggtc agatttgcta accactgagt cacgacagga actcccttat   600
cagctttttct attactctat ttcttgaggg tgttattcac atggtttcag ctattacctt   660
tttgctttac ctatatctca tgcctgcata tttcagattc atcatccaat attggaaaaa   720
gctttgactg aacaaattct gcttataaca aatagtacta gaacactttg catagatcat   780
atattactcc tcacccaggg ttgtcttata aaatttctgt ggatgaaatt ctcactttga   840
tatataaaaa tggcaacgct tgggttattc attgcaaaag cttggtttgc ccatatggca   900
ctttgctcct tactggtcat tatgctctga ggcttacctg gccagtggca cctgatgtta   960
tcttaaatct ctggctttc aactctcccct tgggcaagtc ttttttctctg gtgtattgtt  1020
agtgatttcc ttgatcaagg ttttacctac ttttctggcc caatcaagtc cataactgta  1080
tctattcata taattcaaaa ttggtgagcg atagtcataa gggaatgttg tatttattgc  1140
acaataggta aagcatcttg ctgagaaaac acaaaggaag tatcaaatgg ttagggcaca  1200
cttgcttttg tattccttttt cttagaaatt atactctttt gcctatggcc ttggcaacca  1260
agagctaaca cataaaggca cagtgaacag ccaagacctt ttctagttat acctatgaca  1320
ctggggtcat ttcatcattt cttttcatgg cttcctcctg gctccatatg aacactctta  1380
gaattaatat tagctgaata atttgaatac acagtagaca ctgagttggg tttctgagga  1440
atacaaaacc tatatgacag tcaggaatat tctcctccca catacatcta gcatgatatg  1500
aatgcaaggt atcttatgaa gaaaaatcat taattatgcc gatactctac ttgcttactt  1560
cataacagca tctatctatc tatacttaag tactgaatat atctttacag gcaatgaata  1620
gaagaaataa agataaaaat gagtagtcta atacaatcag ccaattacat ttatgaacat  1680
ctatcactaa agaggcaaag aaacttgaag acaacttttta tacgtgggca actaagaaat  1740
acttttgagg cctggctcag actctattat agcacgttag gtgagaccct cctcctgtct  1800
gggctttcat cttctttctt ccttccatca tttggccttc atgaatatta gctgacatac  1860
attgattcac tatagaagat atgagaccaa acttgagagg attgatttgt ttttcttttc  1920
tttctttctt cttcttcttc ttctttttttt ttttttttttt ttttttttttt ttaaggctgc  1980
```

```
acccaaagca catggaagtt tccaggccag gggtcaaatc aaagttgcag ctgtggtcta    2040
taccacagcc atagcaacac cagatctgag ctgcacctga gaccaaggtc tcttgtggcg    2100
atgcggattc ttaacccact gagcaaggcc agggattgaa cctgcatcct catggacacc    2160
atgttttgtt cttgacccgc tgagccacaa agggaattcc taaaagcacc actttaataa    2220
atttgtacca gtatcatttt tttctctaaa aatattctct aaatgttact ttctgtctta    2280
aaacccttca aaaagtcctc actatctaga gaataaaatt tgcactcctt aaaattcttt    2340
gcccactgtt atgtcacccc tttgtctttc ttctcatctc catctactcg ctactccttg    2400
cacttcataa cctaaaattca ctatttgatt tagttgtagt gactttgtta tcatgttcaa    2460
gaccatatac ttcctttcgt tttagcctac atctctcttt cttccttagg tctgagctgt    2520
catcacaggc ttgtcatgtc attttctcca ttatggcata aaatggtaac atctatttag    2580
ttagcatgaa atagtgacct tcgtgtggcc tgtgtatctc caatacctat tagaatttcc    2640
ccacaagaaa gctcttgaaa acctaccaag tgctaaagag accttattgt ggctaccata    2700
acttggggac tgggccagaa tgtcactgtc ccccagccaa cgtctgtact tattgaacag    2760
tttcatttcc tggatggatt ttctttatca gatggtaaat tatccacttg ttaaaatgct    2820
cctcagaatt tctggggata gataatagga agaaatcatt ttctaatcat gcagatttct    2880
tggaattcaa actcactatt gattttattt tccaaccaca caattagcat gtcattaaat    2940
actgtataaa aatagccaca gaagtggatg attatccatt cacctcctcc ttcacttctt    3000
gtcctccact ttggagaaaa ggtaagaatt tcagattcaa ttcaatgtat cctctcatcc    3060
tgatcttaaa ctacgttgag atatagaaag aacatagttg cttaaaaata tgtatttaat    3120
atatagggta tttgtgggta tttaagatag tgctgatact atttttcagta cttagtttaa    3180 aaaaatagaa gtgcctgtaa agatttgata aaaatttaaa tgaccgtgtt gtatgaatct    3240
aacaaaatgt agtaatggtg actgctattt cctttagtaa aagactagtt aacaggctgt    3300
attaaaagat acatttcttg aattatatgt ctctcaaatt gattaaacat accacagcca    3360
taaaggcaaa tacatttaat ttatagcatg ggtatatgaa taatcattat taagaaaatt    3420
ttagcccaca aatagtttat agatgttgca tgtcagtcaa gaaatggaga gatttgtttg    3480
ggaacatgtg ctccttaaaa tatttataaa taatatttttt agaagaagag catatttgtc    3540
agaattgttt aaaatatcca aattctcaat ttaccattta tattatgata tttcaaaact    3600
attaaaatag attcataaaa tacagaatta aattaaagac aaacaaaatg tttactttgt    3660
gaaaaaaaaa aaatcctagg gggaacagag tttatctggg aacaaaaaag aaggaaaaca    3720
tgatctgaaa taaagaatag tttaaaattc atggagttcc agttgtggct cagtggtaat    3780
gaaccctact agtatccatg aggacatggg tttgatccct ggacctgctc agtgggttaa    3840
ggatccagca ttgctgtggc tgtggcatgg gccagcagct acagcttcaa ttcaatccct    3900
agcctaggaa tttcaatatg ccaaaaaaaa aaaaaaaaa aggcaataat aaaaatcctg    3960
gcttaaaaat ttataaataa aattataatt ataaataaa gaacatgtaa taatatcttc    4020
cctacttgta aagaattcta ataaagtact atattctttt tttcagtctc tacagtaaaa    4080
aatatttgga aatgtttgag aatttctgca taaagtaaaa tcaataagga ataagacagc    4140
acccatgaga aaaatctagg gcgaaaagtc ttaatttagt aaaaatcttg gattgaagat    4200
tgcgtgtcaa gggatattgg tggcacaaac attatttttt ttacaaaact tttagaaatg    4260
cagtaaaatc taccattttag tacatttttgg tcaaaagtat taacatattt tatgctatgc    4320
agccaggaga agtagcctag agtggggaag tagcctggag tggggaagta gcctggagtg    4380
```

-continued

```
gggaggtagc ctggagtggg gagatagcct ggagtggtaa gcagcctaga gtggggattg   4440
ggcaagtgaa cctgaccttt tggtaaatca tcaagagaca agtgcacaca tgttcacaga   4500
gatgaaagaa ggagagtgta taatctccac aattatgtgg cacaaaggag aagagatgct   4560
gttaggtatg ggggattagg actgtgaggt ggatatatat ggagaagaaa caaaccattc   4620
cgcccaagaa aacatctgga taagtggagc aagtaaacga aatactaaaa tgaaaagctc   4680
agtcttatgg aaataaaaag ctatgtataa gccaattatc catataaatc atttagttca   4740
ataaagctaa aataaaatat gaccttcttt gtatgcattt tatctgataa cttttcctctc   4800
tgtagaactg aggctccaat agggctgaga ccttactatt ttgttcactg ctaacattcc   4860
agcacataag caaagtctgg caataaaaag tgctaaataa taagcactga gaaactgctg   4920
tacagcacag agaactctat ccaatcactt gtgataaaac atgatagaag ataatatgag   4980
aaaagaatg tttacatatg tatgactggg tcactttgct gtagagcaga aatcgacaga   5040
acattgtaaa tcaactgtac ttcaatttta aaaattttta aaaggtgcca aataaatatt   5100
tttgaatcta ttaattaagc tttctgtcaa tatttgtagc ttctgtattt caaaagaaaa   5160
aactaatatg tactgtgaaa tgagatgaaa aagattgaag taggataagg ctgttagtgg   5220
aaaaaatctg aatggctggc aatgaaatag gaacttgaca tgtaagatta aggagtcata   5280
gtagatgttg accctggtc                                                5299
```

<210> SEQ ID NO 4
<211> LENGTH: 4920
<212> TYPE: DNA
<213> ORGANISM: Sus scrofa
<220> FEATURE:
<221> NAME/KEY: promoter
<222> LOCATION: (1)..(4920)
<223> OTHER INFORMATION: Pig beta casein promoter 4.9kb

<400> SEQUENCE: 4

```
agttgtagct gctgacctac accacagcca cagccacgca ggatcctatc tgcatgggtg     60
ctggtcagat ttgctaacca ctgagtcacg acaggaactc ccttatcagc ttttctatta    120
ctctatttct tgagggtgtt attcacatgg tttcagctat taccttttg ctttacctat     180
atctcatgcc tgcatatttc agattcatca tccaatattg gaaaaagctt tgactgaaca    240
aattctgctt ataacaaata gtactagaac actttgcata gatcatatat tactcctcac    300
ccagggttgt cttataaaat ttctgtggat gaaattctca ctttgatata taaaaatggc    360
aacgcttggg ttattcattg caaaagcttg gtttgcccat atggcacttt gctccttact    420
ggtcattatg ctctgaggct tacctggcca gtggcacctg atgttatctt aaatctctgg    480
cttttcaact ctcccttggg caagtctttt tctctggtgt attgttagtg atttccttga    540
tcaaggtttt acctactttt ctggcccaat caagtccata actgtatcta ttcatataat    600
tcaaaattgg tgagcgatag tcataaggga atgttgtatt tattgcacaa taggtaaagc    660
atcttgctga gaaaacacaa aggaagtatc aaatggttag ggcacacttg cttttgtatt    720
cctttttctta gaaattatac tcttttgcct atggccttgg caaccaagag ctaacacata    780
aaggcacagt gaacagccaa gaccttttct agttataacct atgacactgg ggtcatttca    840
tcatttcttt tcatggcttc ctcctggctc catatgaaca ctcttagaat taatattagc    900
tgaataattt gaatacacag tagacactga gttgggtttc tgaggaatac aaaacctata    960
tgacagtcag gaatattctc ctcccacata catctagcat gatatgaatg caaggtatct   1020
tatgaagaaa aatcattaat tatgccgata ctctacttgc ttacttcata acagcatcta   1080
```

-continued

```
tctatctata cttaagtact gaatatatct ttacaggcaa tgaatagaag aaataaagat    1140
aaaaatgagt agtctaatac aatcagccaa ttacatttat gaacatctat cactaaagag    1200
gcaaagaaac ttgaagacaa cttttatacg tgggcaacta agaaatactt ttgaggcctg    1260
gctcagactc tattatagca cgttaggtga gaccctcctc ctgtctgggc tttcatcttc    1320
tttcttcctt ccatcatttg gccttcatga atattagctg acatacattg attcactata    1380
gaagatatga gaccaaactt gagaggattg atttgttttt cttttctttc tttcttcttc    1440
ttcttcttct tttttttttt tttttttttt tttttttttaa ggctgcaccc aaagcacatg    1500
gaagtttcca ggccaggggt caaatcaaag ttgcagctgt ggtctatacc acagccatag    1560
caacaccaga tctgagctgc acctgagacc aaggtctctt gtggcgatgc ggattcttaa    1620
cccactgagc aaggccaggg attgaacctg catcctcatg gacaccatgt tttgttcttg    1680
acccgctgag ccacaaaggg aattcctaaa agcaccactt taataaattt gtaccagtat    1740
catttttttc tctaaaaata ttctctaaat gttactttct gtcttaaaac ccttcaaaaa    1800
gtcctcacta tctagagaat aaaatttgca ctccttaaaa ttctttgccc actgttatgt    1860
cacccctttg tctttcttct catctccatc tactcgctac tccttgcact tcataaccta    1920
aattcactat ttgatttagt tgtagtgact tgttatcat gttcaagacc atatacttcc    1980
tttcgtttta gcctacatct ctctttcttc cttaggtctg agctgtcatc acaggcttgt    2040
catgtcattt tctccattat ggcataaaat ggtaacatct atttagttag catgaaatag    2100
tgaccttcgt gtggcctgtg tatctccaat acctattaga atttcccccac aagaaagctc    2160 ttgaaaacct accaagtgct aaagagacct tattgtggct accataactt ggggactggg    2220
ccagaatgtc actgtccccc agccaacgtc tgtacttatt gaacagtttc atttcctgga    2280
tggattttct ttatcagatg gtaaattatc cacttgttaa aatgctcctc agaatttctg    2340
gggatagata ataggaagaa atcatttttct aatcatgcag atttcttgga attcaaactc    2400
actattgatt ttattttcca accacacaat tagcatgtca ttaaatactg tataaaaata    2460
gccacagaag tggatgatta tccattcacc tcctccttca cttcttgtcc tccactttgg    2520
agaaaaggta agaatttcag attcaattca atgtatcctc tcatcctgat cttaaactac    2580
gttgagatat agaagaaca tagttgctta aaaatatgta tttaatatat agggtatttg    2640
tgggtattta agatagtgct gatactattt tcagtactta gtttaaaaaa atagaagtgc    2700
ctgtaaagat ttgataaaaa tttaaatgac cgtgttgtat gaatctaaca aaatgtagta    2760
atggtgactg ctatttcctt tagtaaaaga ctagttaaca ggctgtatta aaagatacat    2820
ttcttgaatt atatgtctct caaattgatt aaacatacca cagccataaa ggcaaataca    2880
tttaatttat agcatgggta tatgaataat cattattaag aaaattttag cccacaaata    2940
gtttatagat gttgcatgtc agtcaagaaa tggagagatt tgtttgggaa catgtgctcc    3000
ttaaaatatt tataaataat attttagaa gaagagcata tttgtcagaa ttgtttaaaa    3060
tatccaaatt ctcaatttac catttatatt atgatatttc aaaactatta aaatagattc    3120
ataaaataca gaattaaatt aaagacaaac aaaatgttta ctttgtgaaa aaaaaaaat    3180 cctaggggga acagagttta tctgggaaca aaaaagaagg aaaacatgat ctgaaataaa    3240
gaatagttta aaattcatgg agttccagtt gtggctcagt ggtaatgaac cctactagta    3300
tccatgagga catgggtttg atccctggac ctgctcagtg ggttaaggat ccagcattgc    3360
tgtggctgtg gcatgggcca gcagctcag cttcaattca atcccctagcc taggaatttc    3420 aatatgccaa aaaaaaaaa aaaaaaggc aataataaaa atcctggctt aaaaatttat    3480
```

```
aaataaaatt ataattataa aataaagaac atgtaataat atcttcccta cttgtaaaga    3540
attctaataa agtactatat tctttttttc agtctctaca gtaaaaaata tttggaaatg    3600
tttgagaatt tctgcataaa gtaaaatcaa taaggaataa gacagcaccc atgagaaaaa    3660
tctagggcga aaagtcttaa tttagtaaaa atcttggatt gaagattgcg tgtcaaggga    3720
tattggtggc acaaacatta ttttttttac aaaactttta gaaatgcagt aaaatctacc    3780
atttagtaca ttttggtcaa aagtattaac atattttatg ctatgcagcc aggagaagta    3840
gcctagagtg gggaagtagc ctggagtggg gaagtagcct ggagtgggga ggtagcctgg    3900
agtggggaga tagcctggag tggtaagcag cctagagtgg ggattgggca agtgaacctg    3960
accttttggt aaatcatcaa gagacaagtg cacacatgtt cacagagatg aagaaggag     4020 agtgtataat ctccacaatt atgtggcaca aaggagaaga gatgctgtta ggtatggggg    4080
attaggactg tgaggtggat atatatggag aagaaacaaa ccattccgcc caagaaaaca    4140
tctggataag tggagcaagt aaacgaaata ctaaaatgaa aagctcagtc ttatggaaat    4200
aaaaagctat gtataagcca attatccata taaatcattt agttcaataa agctaaaata    4260
aaatatgacc ttcttttgtat gcattttatc tgataacttt cctctctgta gaactgaggc    4320
tccaataggg ctgagacctt actattttgt tcactgctaa cattccagca cataagcaaa    4380
gtctggcaat aaaaagtgct aaataataag cactgagaaa ctgctgtaca gcacagagaa    4440
ctctatccaa tcacttgtga taaaacatga tagaagataa tatgagaaaa agaatgttta    4500
catatgtatg actgggtcac tttgctgtag agcagaaatc gacagaacat tgtaaatcaa    4560
ctgtacttca attttaaaaa attttaaaag gtgccaaata aatattttg aatctattaa      4620 ttaagctttc tgtcaatatt tgtagcttct gtatttcaaa agaaaaaact aatatgtact    4680
gtgaaatgag atgaaaaaga ttgaagtagg ataaggctgt tagtggaaaa aatctgaatg    4740
gctggcaatg aaataggaac ttgacatgta agattaagga gtcatagtag atgttgaccc    4800
tggtcatatg acaaaatttc tatcagacat ttttattaca cctttggttt cttttagagg    4860
aaataaaata agaaatatat tagattgacc agtcatatac attttttccc tcatttcccc    4920
```

<210> SEQ ID NO 5
<211> LENGTH: 5012
<212> TYPE: DNA
<213> ORGANISM: Artificial Sequence
<220> FEATURE:
<223> OTHER INFORMATION: 3'arm of porcine beta casein gene

<400> SEQUENCE: 5

```
ctgcacttca ttctcctgga taagcctaaa ataaaggcaa attccatcaa tatggcaacc      60
taattattaa ttatcaattt attctcattg attgattatt tactgaatct tttaattagc     120
tatgaatctt ttctatttca aatcattcaa aattgtattt atgtactgtt ggcagatttg     180
attggttttc tttcagttgc ctatacactt acacttgatt ttcatcattg ttatggaaaa     240
ctaaaaataa tttattttac ttttatgtaa atatagtaga gctatttaa agaccaactg       300 cattcacatt tcttacttag gctttatgaa cttcaagtat ttttaatctc atttaaaatg     360
tataaatttt ctcttaattc atgagtcaaa atgcagttca ctagtccaga tataaagctt     420
aaaaaaggaa gtcaatacag ttttgagatt cttaaaacac acaccctttt gtgatcatga    480
tatagtaaac atttaataa aacaattcta ggtgagatga tatttttttcc tagaggaact      540 tttatatgcc tccaagatag ggcacagcat ggaacatttg taataaaatt tctcttatga    600
attagtcata tcagaattac agaggggaag agattagttt tataacataa ttaattctat    660
```

```
atttgttctc tattccgcag aattgactgt gactggaaat gtgacaactt ttcaatcttt      720
gcatcatgct accaaataat ttttaaatga gtctacatga aaaaaatgaa actttattct      780
cttatttatt ttatgcttta tatggccttc atcttaattt gaatttgact cagaaattct      840
ctattttcaa aattttaatt caactaatag cacagaattt caattttgag ttggaaatac      900
catgaatatt tcaaaaatat gtataaaaat aatttatgga attataattt cctaaccagt      960
catttcaata aattaatcct taggcatatt taagtttcct gtttttatta aattttcca      1020 aacctaactg gcctctttat tagttaactt aaagttatta ttaatgttaa aaatagccac     1080
ggaaaaattg aaattgagta gaatgctttg acttgagtac taaattatat caaaaatgga     1140
ggaaaaggca gggtgatcta atgctgaata tactctagaa agtcttggtt tatacctctt     1200
atctcagctg aactattata cttgtgcctt tcactctcaa aagtatctgc attggatgtt     1260
aaattttatg atcctcctag ataagaaggc ttccaatgta aaatctgaat cacggctctg     1320
taacatggtg gctaaatggt gctgtataag ttaggctttc aaagattcag ttttttgcatc    1380 tataacacag tcagttgaaa gggttttatt gaagttttaa tgtgaatagc ccccacaca      1440 gtgcaggatg ggtgtccgtg tggctccaca ttcctcactt acactagagc agccagtgcc     1500
agtgtcacaa tgagaatgag ctgaaggatg ttgttttagc cactaatgcc caagagagta    1560
gacttatgtg aagctctgat atcccttgtc tctgtctgtg gagtaatttt ttcattgcaa    1620
tgaattatct gtctaccaac tatcaccgaa gtatcggctg cctctataca ctgacgccaa    1680
atagaaatgt ggaaaccggc aaaagtagct ttaattgcca ggcagagggt acacagcagg    1740
ctagtgcttc gaggactgtg tgcctcttgg aggagtggtg aggactctta ctcttactct    1800
tcaaggagcc gggcatgatc agcccttgga tatttttccta actgtttggt gatgaggtaa    1860
ttgggagtca gcatcatcaa ccttctgttt ccaactggtc tggggtctac atgtttgtgg    1920
gcagcatgca gttgacttct tccgcctggt aggggtttga gcacctgcaa aaccgttcca    1980
aggacatggc tcagcatatt atctatagtc catgaggaag aaccataagt ccttgacatt    2040
gctgagtggc taaactatta ttactctgtc ttgcttgact gtattccttt ttctctgtat    2100
tttctcactt ctctgatcaa actgattctt tgactaaagt ttttctatag acaaaaatgc    2160
aggcagagga caagagtgtg gatccactgt gggaaggctt cacagggtcc tgcttggtta    2220
cacaactcct acatttgtaa acttgattcc ctccccttgt gtttacacaa ggacttgttt    2280
ctagcagtaa tttcatcttt cctgcatcct cagtgttttc cttacctcag gatcaagtgc    2340
aagccatact taggctataa tatctcccat ctttaaagaa aaaattccat ccttggcagt    2400
actttagact gctctatggt aaccatcaga aaggaagtgt ccaaactact gtgtctattg    2460
tttcacatgg tattctctca tcaacctgtt cccattgagc tttaccccta tggtaaccac    2520 tttttttcaag attaccaaca acattcattt taccaatcta tgtttatttt acccaaacta    2580
tcagtgctat ttggtccagt tgatcattcc tttttttttt tttttttttt gaaatatcgc    2640
aaatttattt tgaaatccta agcctgataa gcccttgatt tccctcttaa ctcaccagtt    2700
atttctttgc atcgtctctt ctggcatttt ctccttttcc aaacatgcaa tgtgtggaat    2760
accctaggga ttagccttac tatgattgat gttgtttgat tccatgactt taagtccatt    2820
catgggcttg aagcttccac atgtatgtcc tcaaacttat tttttcctga actccaaatt    2880
caagtgctca actgcattct tctccacatc ggagtatcta attaatatct caaacctgac    2940
atggccagca gaacttttg tctgaatcca gtccccaaat tgtccaaaat ttaattgggc     3000
atatttcaat aacaaaggca actaatataa tagtgcacaa gcaatatctt tgaatgggca    3060
```

```
cttcaccaaa gaggttattt taattgtcaa taaatatatg aaagatgtt caataccatt    3120
atttctctgg aaaatgcaag ttaaaaatac cagatatcat gacacaacct ccagaatagc    3180
tgaatgagaa gaattggtaa accaagtat ttacaaaaat aagcaaactg aataaatgct    3240
aggtaatgtt aaaataaata taaatggtt caagcaactc ggaaagtatt atgagtcttt    3300
gtcaaaaata aacatctgct tatattataa ctaacatttc ttctcttagg tatacaacca    3360
aaaggaaacc ataatatgct ttcatatgta ttctaaaaac atttacccaa tactcctaac    3420
aatgctaata ccctaaacta aaatcaacat aaatgtgaat taacatttac gttattttgt    3480
ataaatttgt attttgtata aatgtatttt gtataaataa gtcatggtct aaagtggaat    3540
gggatatcat actgcagttg aaatgaatga gttactgcca caaaaaaaca agggtgaatt    3600
ttatataaat aacattgaat gacagtaatc aggccaaaat ataatggaat atgtaatcca    3660
ataagtggaa tttattagaa tctaatgatc gattaaattc ttgtgtgata agctagacta    3720
ttggttatct gagggaaggt acaacttgac agaaaatgtg agaaagtgct ggggaactag    3780
cgatattctt tcccttagcc tggaagtaag tatctgtggt gattcattgt gatgtgtgca    3840
ttcagtatat tgcctgtctt cttccttttc cctgtggttg ggacctcatc aatgcagact    3900
caccttctttg ctgttggact tgaatgggat tgtgtactat agcacaggac cgggtttcct    3960
cagaaactgt aatagttggt taatgctact gttatatgca tagttttagc ccccactgag    4020
gtgaaaattt cagaatgaga agcaggagat gagagagaac ttgcagatga attctccttt    4080
tttttttttt tttttttttt gctgtatatt acagcgaggt ggtaatcaca caagacctaa    4140
cattttttgat agttaaagga gacccataca gtttacacta acagaacagc tttattacag    4200
gcagaggaca gagtacaaca acaggagaag ggtatgcatt gaaagatgaa agaggtactg    4260
agatctcaag agcaaacttc atttatcctc ctactgcttg gtagcacaag acatgtgtta    4320
tcttcagttc ttaggccact aacagagggt gtgcaaagca cctcaatact aggaagctca    4380
aaatgacttg tgagatctct tacaataagc tcatcaagca ggcatatttt agctatataa    4440
tgagtcaaca attgaatgcc aaaccccatt ttacttcacc actcctagat tctcctaaat    4500
ctggtgtaaa ccacatccac ttattactaa acaatgttta ccagccagta catcctgccc    4560
atagcaactc acagacatac agttacaaat aacatttacc aagatccagg tgccagcaga    4620
tcctgtgtcc ggtgaaggct ccctcttggc ctgcaggtgc ctgcctttct gctgtatcct    4680
cacaaggcag aaagatagac aagctctctc ctagcttttc ttagaggggc actaatccca    4740
ctcatagata tcccactcac atgacctatt tgcctccaaa gatgccacct ccaagtgcat    4800
cacatggggg agttagggct tcaacatatg aattcgggag ggcatgcaaa atctaatcta    4860
tagtgattaa tatgacatga atccataaaa tggatagttc ttgtgaaagt taggacaata    4920
ggaacccaac tattgaaagt ggaatatatg ggaaggtatg gaaaatttac agaaccgcct    4980
gctcccaagt gctcctgaag gtcttactgt aa                                  5012
```

<210> SEQ ID NO 6
<211> LENGTH: 21
<212> TYPE: DNA
<213> ORGANISM: Artificial Sequence
<220> FEATURE:
<223> OTHER INFORMATION: 6 pig beta casein 586 bp forward primer

<400> SEQUENCE: 6
tcttgaaaac ctaccaagtg c                                              21

<210> SEQ ID NO 7

```
<211> LENGTH: 21
<212> TYPE: DNA
<213> ORGANISM: Artificial Sequence
<220> FEATURE:
<223> OTHER INFORMATION: pig beta casein 586 bp reverse primer

<400> SEQUENCE: 7
attcgtacaa cacggtcatt t                                              21

<210> SEQ ID NO 8
<211> LENGTH: 22
<212> TYPE: DNA
<213> ORGANISM: Artificial Sequence
<220> FEATURE:
<223> OTHER INFORMATION: ATG UP forward primer

<400> SEQUENCE: 8
agagaactct atccaatcac tt                                             22

<210> SEQ ID NO 9
<211> LENGTH: 20
<212> TYPE: DNA
<213> ORGANISM: Artificial Sequence
<220> FEATURE:
<223> OTHER INFORMATION: ATG UP reverse primer

<400> SEQUENCE: 9
gcaaggatga ggagcttcat                                                20

<210> SEQ ID NO 10
<211> LENGTH: 20
<212> TYPE: DNA
<213> ORGANISM: Artificial Sequence
<220> FEATURE:
<223> OTHER INFORMATION: ATG down forward primer

<400> SEQUENCE: 10
atgaagctcc tcatccttgc                                                20

<210> SEQ ID NO 11
<211> LENGTH: 21
<212> TYPE: DNA
<213> ORGANISM: Artificial Sequence
<220> FEATURE:
<223> OTHER INFORMATION: ATG down reverse primer

<400> SEQUENCE: 11
tctgctggag atttagggaa g                                              21

<210> SEQ ID NO 12
<211> LENGTH: 21
<212> TYPE: DNA
<213> ORGANISM: Artificial Sequence
<220> FEATURE:
<223> OTHER INFORMATION: 3'down forward primer

<400> SEQUENCE: 12
cttccctaaa tctccagcag a                                              21

<210> SEQ ID NO 13
<211> LENGTH: 21
<212> TYPE: DNA
<213> ORGANISM: Artificial Sequence
<220> FEATURE:
<223> OTHER INFORMATION: 3'down reverse primer

<400> SEQUENCE: 13
```

```
gttgtcacat ttccagtcac a                                            21
```

```
<210> SEQ ID NO 14
<211> LENGTH: 527
<212> TYPE: DNA
<213> ORGANISM: Artificial Sequence
<220> FEATURE:
<223> OTHER INFORMATION: ATG up 0.5kb sequence

<400> SEQUENCE: 14
agagaactct atccaatcac ttgtgataaa acatgataga agataatatg agaaaaagaa      60
tgtttacata tgtatgactg ggtcactttg ctgtagagca gaaatcgaca gaacattgta     120
aatcaacctg tacttcaatt ttaaaaaatt ttaaaaggtg ccaaataaat atttttgaat     180
ctattaatta agctttctgt caatatttgt agcttctgta tttcaaaaga aaaaactaat     240
atgtactgtg aaatgagatg aaaaagattg aagtaggata aggctgttag tggaaaaaat     300
ctgaatggct ggcaatgaaa taggaacttg acatgtaaga ttaaggagtc atagtagatg     360
ttgaccctgg tcatatgaca aaatttctat cagacatttt tattcaccct tggtttctt      420 ttagaggaaa taaataaga aatatattag attgaccagt catatacatt ttttccctca      480 tttcccatt cacaggactt gatcgccatg aagctcctca tccttgc                    527
```

```
<210> SEQ ID NO 15
<211> LENGTH: 3976
<212> TYPE: DNA
<213> ORGANISM: Artificial Sequence
<220> FEATURE:
<223> OTHER INFORMATION: ATG down 4kb sequence

<400> SEQUENCE: 15
atgaagctcc tcatccttgc ctgcttcgtg gctcttgccc ttgcaagagc ggtaagtaca      60 gaaaaaaat ctctgaataa ataaggaata gtactacctg cctatgggta gaaaatggta     120
ttaccaacac tgtaaaggta taaataatgc agaagagcag gtttgttttt gtttgtttat     180
tttttcactt ctaagaaaat tccttgtatt cacccaccat ctcaacaata tccactgggg     240
ccacacatct ggatcaaatg cttcctgtag tattgtgcca ccagtgccta aggtaaacaa     300
gcaaaccaat aagcaacaga taaacaagaa gaaacacata tgagaacaat aaaaagagta     360
atattacaca aatacacttc catcttcttc cagtgatgaa atgtatgatc tctagggcac     420
ccagttaaat cctacctgtg tctattgaac agagaatgat actccagaag atggggtatc     480
agacaataat cacaaacata ttcataatca taatgaaagt attcaataca aatgaaaata     540 acttttttt ctgttatcca taaaaaactc ctcattaagg aaaaataaaa atataccagt     600
aaaaagttaa tacatttaaa taatgtaaaa gcaattacaa gtctctcaaa agacatagaa     660
catatttttt cagtttgtga aatagatagc tctgcataag gaaggtaaaa ttcagatagg     720
aaaaatgttt aataatgagt caactatggg gactaaaatg ctggttttc ttttttttct      780 ctatagaagg aagaactcaa tgcatctggt gaggtaagat attttattc agagaaaaat     840 tcccaagcat aaaatagtaa aactttctga tgatctagca gatttagctg gaggttgaat     900
ttcaactttt cctttctttt ttccttttca gactgtggaa agcctttcaa gcagtgaggt     960
aagccaatgt ttattcatag gtaatttccc aaatttagaa ccattaaaaa aactgcacta    1020
tccttctttt agtgtgaaca cgaacatgca ttgatgaagc tatcatatct atattctgac    1080
acttaagttc taatgtaaat ttccattgta tatatttaaa gagagaatac atgtccggag    1140
gatttaacgt tctagccatt tctgagttga ctggctactg gaaattgtgg cactgtgctc    1200
```

```
cgcttcttct tcttttttt taatgaactg tacagtcttt ttttctatct tgatctctct    1260
ctatattaac ctcattcact gttttgacat ttattgatac atttatgtat cagactttaa    1320
ctagagctgc ggtacaaact ggaaagaggg aagcccataa gaaagatctc gcagtgtagt    1380 caggggggcgg atgtgcaaat ggacacattt tgtcattata atagcataat agcagtctag    1440
taaataagag gtagttagac ttagtctagt cctaaatctg cccagggtgt cagtcaggta    1500
gatattaacc ctcacatcac tctttgagtc tgttatcacc tgttagtgaa atggtacatc    1560
actaaacttt gactcttcac aaaggttatg agatcctaga gggaggatat gtatttctta    1620
taattcataa caagcggact aagaatgagt aacaaaggta tcagtgatta tatatataca    1680
cacacatatt tttgtctttt tgccttttct agggctgttc ctgcagcata tggaggttcc    1740
caggttaggg gcctaatcag agctgtagcc gctggcctac accagagcca cagcaatgtg    1800
ggagtgggat ctgagccgca tctgcgacct acaccacaac tcatggcaac gccaaatcct    1860
taacccactg agcaaggcca ggaatcgaac ccacaaactc atggttccta gtcggatttg    1920
ttaaccactg ggccacgaca ggaactctga ttactgtatt ttcaatgact gttattcttt    1980
tcaaatcaga tgggttatta gagatccttt gttattgtaa gaagggtaat agagagaaat    2040
tagtatctgt tacaggcctc tgttgttact atgctcactc atttttcttc cttttatgac    2100
tgcatcatct gttcttcttt tatacaatag atttattcag aatagtgtaa cataaatttc    2160
cagcaattaa aataatatta tcaaacaagg tgtccacatt aacctataaa atgtcatttg    2220
ctgacttata ttgacaaata agaattgttc attaaaactc aatcttattt ttattttcta    2280
aaggaatcta ttactcacat cagcaaggta aagacttcat ctttaaatac gcctattttc    2340
aaaacttcct gttcacttgt tacaaatagc aacatttatt ttggtgtgat ctgttttcta    2400
ggagaaaatt gagaagctta agcgggagga acaacaacaa acagaggtaa tttgttcatg    2460
atgagcatat tttgaaaatt attattaaac atgatatatg caaatgtttt atatgttcac    2520
tcaaaaacat ggtattaata taaatcagtg taagaaatta aactatgaca aagtgaaaag    2580
attttaaaga catagacaca tttaaataca taatcaactt ccagagtaaa gaataagtac    2640
ctgtgaataa ctattgattt attcatttta ccaacagtat acctgttttc agtaagtgca    2700
cttaatggga acatttccgg ttcggggctg tgatcccctt gatgaaagag tagggaggtg    2760
gtgcaccacg aatcctgatt ggatcctata tcagctgtat aaccctggtc ccaagtttct    2820
ctgtacctca atttcttctt ctgtaaaatt gagaaaattc ataagccaat agggtggatg    2880
agctggcaca cagtgactat ccaatgattt tacgttaaca ttctgtagct tttatactca    2940
tttatgaatg tgtgaaggtc ttaaaaaaat ttccattaca cagttgagaa agtaagata    3000 cagaacaatt gagtacacaa ttgtgtgaca acttgcatag ttattaataa gcagggcttg    3060
cttaaaaaca aggatttgag gatgaaataa aattctttaa ttaaattact cttgtggtaa    3120
catatttatc caatcatgat atttaagctt tcctgtttta ccaatgaagt tggattattt    3180
ggtacttacc ccaaatattt tctaaatcaa aatgaattta caatttatg cctcttttaaa    3240 aactcaagat taccacttta taccaaggga agtagtgctg gaagtttgcc attaagtacc    3300
tccttgaatt aaaaacacaa attaagattt aaacaatata aatcttggag ttatccaagc    3360 ctttttttggg aagaactctt ccttcattat atgaaaacaa tttggtctat tatcaacaca    3420
ttgttgtaaa gtctgtaccc tctgaagacc aaagtaagta gctacagctc cgcaggcagc    3480
tcaggaaaag gtgaaacaaa tcttgacatc tccaaacact gatttccctt ggctctgcgc    3540
attgcctagg aaggaagggg ttagggagca gtccctccat gagcatttta cccagtaatc    3600
```

```
ctcacatggt atgactccta aaccaaaaga agtgaacaat tgttctctt ttcacttaat    3660 tatgagtgtt caaaaaaaga ggccgctaat tcatcatgaa tgacagttgt agctgcatta   3720
cggactcaac gattctttt ccttctttcc agaatgaacg ccagaataaa atccaccagt    3780
ttccccagcc tcagcctcta gcccatcctt acaccgagcc catcccttac cccatccttc   3840
cacaaaacat cctgcctctt gcccaggtcc ctgtggtggt gcctcttctt catcctgaag   3900
taatgaaaga ttccaaagct aaggagacca ttgttcccaa gcgtaaagga atgcccttcc   3960
ctaaatctcc agcaga                                                   3976

<210> SEQ ID NO 16
<211> LENGTH: 1725
<212> TYPE: DNA
<213> ORGANISM: Artificial Sequence
<220> FEATURE:
<223> OTHER INFORMATION: 3' down 1.7kb sequence

<400> SEQUENCE: 16
cttccctaaa tctccagcag agccttttgt ggaaggccag agcctaactc tcaccgattt     60
tgaagtcctt tctctgcctc tgctccagtc tctgatgcac cagattcccc agcctgttcc   120
tcagaccccc atgtttgctc ctcagcccct gctgtccctg cctcaggcca aagtcctgcc   180
tgttccccag caagtggtgc ccttccccca gagagatatg cccttccagg cccttctgct   240
ctaccaggat cctctacttg gccctctcca agggttctac cctgtgcctc aaccagttgc   300
cccagtttac aaccctgtaa gtccaagttt attcactgtg ctgtttcact tatgatgttt   360
agttgctgtt agagtaatta agcaagaact ctagaataaa agagacaatg aataataagt   420
ggttccaaaa tgcacatagt ttagatagtg attctcaaca tttgctacaa atagaataac   480
caataactgg gagatttcct cccaaatctc aaagtccagg attacccaca aagattcgac   540
ataattgtac ttacctctat atgtagggga aattgaatat tgggaagaga taatttcagg   600
gattatgatt taattggtct gttgagaatt gagataaaga gagaggattt aaggtatact   660
aaagccagaa ttaaatgtaa caatctcatg tggcttggaa taacaaacct aagaaggttt   720
gttattatct gcaattttga agttttcctt atgtgcaatt atttccccac atgcctcatt   780
tcacatcttg tttgatatat gaacatttga gggcaagata ctgagatgcc tatttcaata   840
ctcatggaat actcagggaa attgttcttg ccaaaagatg aactgtatat ttattcgctt   900 ttttatttt taatttttaa ggtctaagag gatttcaaag ttaatgccct ctcctcactt   960
ttggtaagct ttaagagttt gaaaatcaga ttaatcattt ttatagttag tatctttctg  1020
cacttcattc tcctggataa gcctaaaata aaggcaaatt ccatcaatat ggcaacctaa  1080
ttattaatta tcaatttatt ctcattgatt gattatttac tgaatctttt aattagctat  1140
gaatcttttc tatttcaaat cattcaaaat tgtatttatg tactgttggc agatttgatt  1200
ggttttcttt cagttgccta tacttaca cttgattttc atcattgtta tggaaaacta  1260
aaaataattt attttacttt tatgtaaata tagtagagct attttaaaga ccaactgcat  1320
tcacatttct aacttaggct ttatgaactt caagtatttt taatctcatt taaaatgtat  1380
aaattttctc ttaattcatg agtcaaaatg cagttcacta gtccagatat aaagcttaaa  1440
aaaggaagtc aatacagttt tgagattctt aaaacacaca cccttttgtg atcatgatat  1500
agtaaacatt ttaataaaac aattctaggt gagatgatat ttttttcctag aggaactttt   1560 atatgcctcc aagataggc acagcatgga acatttgtaa taaaatttct cttatgaatt   1620
agtcatatca gaattacaga ggggaagaga ttagttttat aacataatta attctatatt  1680
```

```
tgttctctat tccgcagaat tgactgtgac tggaaatgtg acaac            1725
```

<210> SEQ ID NO 17
<211> LENGTH: 21
<212> TYPE: DNA
<213> ORGANISM: Artificial Sequence
<220> FEATURE:
<223> OTHER INFORMATION: sequencing primer

<400> SEQUENCE: 17

```
cctgtgtcta ttgaacagag a                                       21
```

<210> SEQ ID NO 18
<211> LENGTH: 21
<212> TYPE: DNA
<213> ORGANISM: Artificial Sequence
<220> FEATURE:
<223> OTHER INFORMATION: sequencing primer

<400> SEQUENCE: 18

```
agaaggaaga actcaatgca t                                       21
```

<210> SEQ ID NO 19
<211> LENGTH: 22
<212> TYPE: DNA
<213> ORGANISM: Artificial Sequence
<220> FEATURE:
<223> OTHER INFORMATION: sequencing primer

<400> SEQUENCE: 19

```
aatggtacat cactaaactt tg                                      22
```

<210> SEQ ID NO 20
<211> LENGTH: 21
<212> TYPE: DNA
<213> ORGANISM: Artificial Sequence
<220> FEATURE:
<223> OTHER INFORMATION: sequencing primer

<400> SEQUENCE: 20

```
ggtgtgatct gttttctagg a                                       21
```

<210> SEQ ID NO 21
<211> LENGTH: 22
<212> TYPE: DNA
<213> ORGANISM: Artificial Sequence
<220> FEATURE:
<223> OTHER INFORMATION: sequencing primer

<400> SEQUENCE: 21

```
gtgtgacaac ttgcatagtt at                                      22
```

<210> SEQ ID NO 22
<211> LENGTH: 21
<212> TYPE: DNA
<213> ORGANISM: Artificial Sequence
<220> FEATURE:
<223> OTHER INFORMATION: sequencing primer

<400> SEQUENCE: 22

```
gtccaagttt attcactgtg c                                       21
```

<210> SEQ ID NO 23
<211> LENGTH: 21
<212> TYPE: DNA
<213> ORGANISM: Artificial Sequence
<220> FEATURE:

<223> OTHER INFORMATION: sequencing primer

<400> SEQUENCE: 23
tggtgctgta taagttaggc t                                               21

<210> SEQ ID NO 24
<211> LENGTH: 21
<212> TYPE: DNA
<213> ORGANISM: Artificial Sequence
<220> FEATURE:
<223> OTHER INFORMATION: sequencing primer

<400> SEQUENCE: 24
taagtccttg acattgctga g                                               21

<210> SEQ ID NO 25
<211> LENGTH: 20
<212> TYPE: DNA
<213> ORGANISM: Artificial Sequence
<220> FEATURE:
<223> OTHER INFORMATION: sequencing primer

<400> SEQUENCE: 25
ctttgcatcg tctcttctgg                                                 20

<210> SEQ ID NO 26
<211> LENGTH: 21
<212> TYPE: DNA
<213> ORGANISM: Artificial Sequence
<220> FEATURE:
<223> OTHER INFORMATION: sequencing primer

<400> SEQUENCE: 26
acccaatact cctaacaatg c                                               21

<210> SEQ ID NO 27
<211> LENGTH: 21
<212> TYPE: DNA
<213> ORGANISM: Artificial Sequence
<220> FEATURE:
<223> OTHER INFORMATION: sequencing primer

<400> SEQUENCE: 27
cctcagaaac tgtaatagtt g                                               21

<210> SEQ ID NO 28
<211> LENGTH: 20
<212> TYPE: DNA
<213> ORGANISM: Artificial Sequence
<220> FEATURE:
<223> OTHER INFORMATION: sequencing primer

<400> SEQUENCE: 28
cctttctgct gtatcctcac                                                 20

<210> SEQ ID NO 29
<211> LENGTH: 20
<212> TYPE: DNA
<213> ORGANISM: Artificial Sequence
<220> FEATURE:
<223> OTHER INFORMATION: sequencing primer

<400> SEQUENCE: 29
caggatgtcg cttgaacaag                                                 20

<210> SEQ ID NO 30

```
<211> LENGTH: 20
<212> TYPE: DNA
<213> ORGANISM: Artificial Sequence
<220> FEATURE:
<223> OTHER INFORMATION: sequencing primer

<400> SEQUENCE: 30
ggagactagt gtcaccaaac                                                   20

<210> SEQ ID NO 31
<211> LENGTH: 6500
<212> TYPE: DNA
<213> ORGANISM: Artificial Sequence
<220> FEATURE:
<223> OTHER INFORMATION: 6.5kb sequence

<400> SEQUENCE: 31
tgtgactgga aatgtgacaa cttttcaatc tttgcatcat gctaccaaat aattttaaa      60 tgagtctaca tgaaaaaaat gaaactttat tctcttattt attttatgct ttatatggcc    120
ttcatcttaa tttgaatttg actcagaaat tctctatttt caaaatttta attcaactaa    180
tagcacagaa tttcaatttt gagttggaaa taccatgaat atttcaaaaa tatgtataaa    240
aataatttat ggaattataa tttcctaacc agtcatttca ataaattaat ccttaggcat    300
atttaagttt cctgttttta ttataatttt ccaaacctaa ctggcctctt tattagttaa    360
cttaaagtta ttattaatgt taaaaatagc cacggaaaaa ttgaaattga gtagaatgct    420
ttgacttgag tactaaatta tatcaaaaat ggaggaaaag gcagggtgat ctaatgctga    480
atatactcta gaaagtcttg gtttatacct cttatctcag ctgaactatt atacttgtgc    540
ctttcactct caaagtatc tgcattggat gttaaatttt atgatcctcc tagataagaa     600
ggcttccaat gtaaaatctg aatcacggct ctgtaacatg gtggctaaat ggtgctgtat    660
aagttaggct ttcaaagatt cagttttttgc atctataaca cagtcagttg aaagggtttt   720
attgaagttt taatgtgaat agcaccccac acagtgcagg atgggtgtcc gtgtggctcc    780
acattcctca cttacactag agcagccagt gccagtgtca caatgagaat gagctgaagg    840
atgttgtttt agccactaat gcccaagaga gtagacttat gtgaagctct gatatccctt    900
gtctctgtct gtggagtaat ttttttcattg caatgaatta tctgtctacc aactatcacc    960
gaagtatcgg ctgcctctat acactgacgc caaatgaaaa tgtggaaacc ggcaaaagta   1020
gctttaattg ccaggcagag ggtacacagc aggctagtgc ttcgaggact gtgtgcctct   1080
tggaggagtg gtgaggactc ttactcttac tcttcaagga gccgggcatg atcagccctt   1140
ggatattttc ctaactgttt ggtgatgagg taattgggag tcagcatcat caaccttctg   1200
tttccaactg gtctgggtc tacatgtttg tgggcagcat gcagttgact tcttccgcct    1260
ggtaggggtt tgagcacctg caaaaccgtt ccaaggacat ggctcagcat attatctata   1320
gtccatgagg aagaaccata agtccttgac attgctgagt ggctaaacta ttattactct   1380
gtcttgcttg actgtattcc tttttctctg tattttctca cttctctgat caaactgatt   1440
ctttgactaa agttttctta agacaaaaa tgcaggcaga ggacaagagt gtggatccac    1500
tgtgggaagg cttcacaggg tcctgcttgg ttacacaact cctacatttg taaacttgat   1560
tccctcccct tgtgtttaca caaggacttg tttctagcag taatttcatc tttcctgcat   1620
cctcagtgtt ttccttacct caggatcaag tgcaagccat acttaggcta taatatctcc   1680
catctttaaa gaaaaaattc catccttggc agtactttag actgctctat ggtaaccatc   1740
agaaaggaag tgtccaaact actgtgtcta ttgtttcaca tggtattctc tcatcaacct   1800
```

```
gttcccattg agctttaccc ctatggtaac cactttttc aagattacca acaacattca   1860
ttttaccaat ctatgtttat tttacccaaa ctatcagtgc tatttggtcc agttgatcat   1920 tcctttttt tttttttttt tttgaaatat cgcaaatttt atttgaaatc ctaagcctga   1980
taagcccttg atttccctct taactcacca gttattctt tgcatcgtct cttctggcat   2040
tttctccttt tccaaacatg caatgtgtgg aataccctag ggattagcct tactatgatt   2100
gatgttgttt gattccatga ctttaagtcc attcatgggc ttgaagcttc cacatgtatg   2160
tcctcaaact tattttttcc tgaactccaa attcaagtgc tcaactgcat tcttctccac   2220
atcggagtat ctaattaata tctcaaacct gacatggcca gcagaacttt ttgtctgaat   2280
ccagtcccca aattgtccaa aatttaattg ggcatatttc aataacaaag gcaactaata   2340
taatagtgca caagcaatat ctttgaatgg gcacttcacc aaagaggtta ttttaattgt   2400
caataaatat atgaaaagat gttcaatacc attatttctc tggaaaatgc aagttaaaaa   2460
taccagatat catgacacaa cctccagaat agctgaatga aagaattgg taaaaccaag   2520 tatttacaaa ataagcaaa ctgaataaat gctaggtaat gttaaaataa atataaaatg   2580
gttcaagcaa ctcggaaagt attatgagtc tttgtcaaaa ataaacatct gcttatatta   2640
taactaacat ttcttctctt aggtatacaa ccaaaaggaa accataatat gctttcatat   2700
gtattctaaa aacatttacc caatactcct aacaatgcta ataccctaaa ctaaaatcaa   2760
cataaatgtg aattaacatt tacgttattt tgtataaatt tgtattttgt ataaatgtat   2820
tttgtataaa taagtcatgg tctaaagtgg aatgggatat catactgcag ttgaaatgaa   2880
tgagttactg ccacaaaaaa acaagggtga attttatata aataacattg aatgacagta   2940
atcaggccaa aatataatgg aatatgtaat ccaataagtg gaatttatta gaatctaatg   3000
atcgattaaa ttcttgtgtg ataagctaga ctattggtta tctgagggaa ggtacaactt   3060
gacagaaaat gtgagaaagt gctggggaac tagcgatatt ctttcccta gcctggaagt   3120 aagtatctgt ggtgattcat tgtgatgtgt gcattcagta tattgcctgt cttcttcctt   3180
ttccctgtgg ttgggacctc atcaatgcag actcacctct ttgctgttgg acttgaatgg   3240
gattgtgtac tatagcacag gaccgggttt cctcagaaac tgtaatagtt ggttaatgct   3300
actgttatat gcatagtttt agcccccact gaggtgaaaa tttcagaatg agaagcagga   3360
gatgagagag aacttgcaga tgaattctcc tttttttttt tttttttttt tttgctgtat   3420
attacagcga ggtggtaatc acacaagacc taacattttt gatagttaaa ggagacccat   3480
acagtttaca ctaacagaac agctttatta caggcagagg acagagtaca acaacaggag   3540
aagggtatgc attgaaagat gaaagaggta ctgagatctc aagagcaaac ttcatttatc   3600
ctcctactgc ttggtagcac aagacatgtg ttatcttcag ttcttaggcc actaacagag   3660
ggtgtgcaaa gcacctcaat actaggaagc tcaaaatgac ttgtgagatc tcttacaata   3720
agctcatcaa gcaggcatat tttagctata taatgagtca acaattgaat gccaaacccc   3780
attttacttc accactccta gattctccta aatctggtgt aaaccacatc cacttattac   3840
taaacaatgt ttaccagcca gtacatcctg cccatagcaa ctcacagaca tacagttaca   3900
aataacattt accaagatcc aggtgccagc agatcctgtg tccggtgaag ctccctctt   3960 ggcctgcagg tgcctgcctt tctgctgtat cctcacaagg cagaaagata gacaagctct   4020
ctcctagctt ttcttagagg ggcactaatc ccactcatag atatcccact cacatgacct   4080
atttgcctcc aaagatgcca cctccaagtg catcacatgg gggagttagg gcttcaacat   4140
atgaattcgg gagggcatgc aaaatctaat ctatagtgat taatatgaca tgaatccata   4200
```

```
aaatggatag ttcttgtgaa agttaggaca ataggaaccc aactattgaa agtggaatat    4260
atgggaaggt atggaaaatt tacagaaccg cctgctccca agtgctcctg aaggtcttac    4320
tgtaagggga gcatggagaa aaagagaagg aattgggtgt tcaggcaaag agaagaaaat    4380
ttattagaag gaaaaaggag aggctgactg acctttgaga agagtcagcc cccccgccct    4440
tctagcaggg ccttcttata ctctgcagag gggaaattga ttcctgaagc ggggggaaggt    4500 tagtttatag tttatctttc acctgcaggt ggactctggt ggtcacatcg tcatgagaaa    4560
gtcagaggta tctcacggta gggtgcactc ataatcttga gaaagctgga ggtgtgtggt    4620 ccccccctggt cttgtagtct tgggaaaata ggcaccagtg gcaaaaacag gatgtcgctt    4680
gaacaagatg gtcagtctca tgggtcagca tgatgagcca ttttaacaat gagccccatg    4740
taacccctaa cacttactgt gtatttgtca tgatggaatc atgatttctt tgtttactgt    4800
agctaattat taccctaatg tcctacttct cactttcact tcactgtaac tgggattcaa    4860
ccttgattgg actggaagta gaaagtcctt tacttaatga cttaaagtac actatagtac    4920
atagactagt gttagagggg ttgggtctgg ccaataaaga gaaggagact gtgtatttta    4980
tatttaaaaa acactagacc aatatttaaa aataggagag cttacacaca atccacattt    5040
ctagttcacc tagaagtccc caaatttggt tacatttgac ctgtgtattc ctgcacagca    5100
acaatgcatt ggaaggggca gccaatgagg aatgcacata ttcttcagtt cactgtcagc    5160 actgttttt cacaactgta ttttttttctg cttctgttat ttgtaagact ctagaaggca    5220
gtttgacaat cataattgaa agagaaatat ttaaacatcc ataaatagat atgcttagtt    5280
ctaatggccc tgcacttccc tgtgtctaca aaggataaat tattctcctt taaacttttc    5340
cttgaagggt aaacttttat gaaattcttt tgtgctaaac aattgactga gaactctggt    5400
gagaggtgca aagtaattga aattgcattt ccaacctcag ggaaaatgga aggagactag    5460
tgtcaccaaa ccaagtgaca actggtaaaa aagcgttata ggcaaaaaat acatgtttag    5520
gtgttatgca tatatgtgca tatcaattat atatataatc gataagagac agaactgcta    5580
actaaatagg tcgtttaggt tgtggtacaa gagaccttgc cacctgtatt ttatgacctg    5640
gtggaaagaa gtttcttaaa gagtcacagc agatagggtt tgttggggac cctggaataa    5700
actctggaaa gtaaattcca gcagggtttt gagggtatta atgcaagcga ctattgtcat    5760
tttgagaaat aactcttcat tggagttcgg gaggacactg agtattgtgt tactgtatgc    5820
catggtctaa cctattaaat gtttattatc taatctacct aattataaaa gtaagtgtat    5880
aataatcaaa taatcaaatg agtttggctc aaacaggttc tggtgacata aataaacagc    5940
ttagccatgt ttttcaaatt cccagtgcac ccgcaactgt cataccactg ttcttctctg    6000
cagccacacc tatgttctca tggagaatat cctatagaca ggtgacttca aatgaaagat    6060
cctagaccca gcttataacc tgtcagcatc agctaggcat gaagatttac cattttgttc    6120
attgaattgt ggttgaaagt gtaataaaaa tttagtgaaa ataaaatgtt acaggcataa    6180
agactgttaa caggattgtg caaattctgc tgaatggaat aatgacaaaa aataggagtt    6240
gtgccttaaa atgtaattta ttgaaaagaa ggaagaaaaa tctcagtcac tgcacacaat    6300
tatttgaaat gatggcactt acaggagaag caattcaaag gcttttttaaa caaaatttcc    6360 atattgaaat ttagtaaaga cttttaattc cctctgattc agtggtcttc ctactggcat    6420
gatacaactg aaatttagac actaaactgt taggacaact ttgccaaagg aaaaggatta    6480
tatgctatct aaatatagagt                                                6500
```

<210> SEQ ID NO 32

```
<211> LENGTH: 27
<212> TYPE: DNA
<213> ORGANISM: Artificial Sequence
<220> FEATURE:
<223> OTHER INFORMATION: pig beta casein 3.6kb forward primer

<400> SEQUENCE: 32
atcagatgtt attttatgtg gctaatc                                              27

<210> SEQ ID NO 33
<211> LENGTH: 27
<212> TYPE: DNA
<213> ORGANISM: Artificial Sequence
<220> FEATURE:
<223> OTHER INFORMATION: pig beta casein 3.6kb reverse primer

<400> SEQUENCE: 33 attttttagaa gaagagcata tttgtca                                             27

<210> SEQ ID NO 34
<211> LENGTH: 27
<212> TYPE: DNA
<213> ORGANISM: Artificial Sequence
<220> FEATURE:
<223> OTHER INFORMATION: pig beta casein 3.9kb forward primer

<400> SEQUENCE: 34
agggtatttg tgggtattta agatagt                                              27

<210> SEQ ID NO 35
<211> LENGTH: 27
<212> TYPE: DNA
<213> ORGANISM: Artificial Sequence
<220> FEATURE:
<223> OTHER INFORMATION: pig beta casein 3.9kb reverse primer

<400> SEQUENCE: 35
aatggtacat cactaaactt tgactct                                              27

<210> SEQ ID NO 36
<211> LENGTH: 28
<212> TYPE: DNA
<213> ORGANISM: Artificial Sequence
<220> FEATURE:
<223> OTHER INFORMATION: pig beta casein 4.2kb forward primer

<400> SEQUENCE: 36
tctctctcta tattaacctc attcactg                                             28

<210> SEQ ID NO 37
<211> LENGTH: 27
<212> TYPE: DNA
<213> ORGANISM: Artificial Sequence
<220> FEATURE:
<223> OTHER INFORMATION: pig beta casein 4.2kb reverse primer

<400> SEQUENCE: 37
ccttttgtga tcatgatata gtaaaca                                              27

<210> SEQ ID NO 38
<211> LENGTH: 26
<212> TYPE: DNA
<213> ORGANISM: Artificial Sequence
<220> FEATURE:
<223> OTHER INFORMATION: pig beta casein 3.3kb forward primer

<400> SEQUENCE: 38
```

-continued cagttgccta tacacttaca cttgat    26

<210> SEQ ID NO 39
<211> LENGTH: 25
<212> TYPE: DNA
<213> ORGANISM: Artificial Sequence
<220> FEATURE:
<223> OTHER INFORMATION: pig beta casein 3.3kb reverse primer

<400> SEQUENCE: 39
agtcatggtc taaagtggaa tggga    25

<210> SEQ ID NO 40
<211> LENGTH: 27
<212> TYPE: DNA
<213> ORGANISM: Artificial Sequence
<220> FEATURE:
<223> OTHER INFORMATION: pig beta casein 3.8kb forward primer

<400> SEQUENCE: 40
aactaacatt tcttctctta ggtatac    27

<210> SEQ ID NO 41
<211> LENGTH: 29
<212> TYPE: DNA
<213> ORGANISM: Artificial Sequence
<220> FEATURE:
<223> OTHER INFORMATION: pig beta casein 3.8kb reverse primer

<400> SEQUENCE: 41
aaaggattat atgctatcta atatagagt    29

<210> SEQ ID NO 42
<211> LENGTH: 232
<212> TYPE: PRT
<213> ORGANISM: Sus scrofa
<220> FEATURE:
<221> NAME/KEY: PEPTIDE
<222> LOCATION: (1)..(232)
<223> OTHER INFORMATION: amino acid of porcine beta casein

<400> SEQUENCE: 42

Met Lys Leu Leu Ile Leu Ala Cys Phe Val Ala Leu Ala Leu Ala Arg
 1               5                  10                  15

Ala Lys Glu Glu Leu Asn Ala Ser Gly Glu Thr Val Glu Ser Leu Ser
            20                  25                  30

Ser Ser Glu Glu Ser Ile Thr His Ile Ser Lys Glu Lys Ile Glu Lys
        35                  40                  45

Leu Lys Arg Glu Glu Gln Gln Gln Thr Glu Asn Glu Arg Gln Asn Lys
    50                  55                  60

Ile His Gln Phe Pro Gln Pro Gln Pro Leu Ala His Pro Tyr Thr Glu
65                  70                  75                  80

Pro Ile Pro Tyr Pro Ile Leu Pro Gln Asn Ile Leu Pro Leu Ala Gln
                85                  90                  95

Val Pro Val Val Val Pro Leu Leu His Pro Glu Val Met Lys Asp Ser
            100                 105                 110

Lys Ala Lys Glu Thr Ile Val Pro Lys Arg Lys Gly Met Pro Phe Pro
        115                 120                 125

Lys Ser Pro Ala Glu Pro Phe Val Glu Gly Gln Ser Leu Thr Leu Thr
    130                 135                 140

Asp Phe Glu Val Leu Ser Leu Pro Leu Leu Gln Ser Leu Met His Gln
145                 150                 155                 160

```
Ile Pro Gln Pro Val Pro Gln Thr Pro Met Phe Ala Pro Gln Pro Leu
                165                 170                 175

Leu Ser Leu Pro Gln Ala Lys Val Leu Pro Val Pro Gln Gln Val Val
            180                 185                 190

Pro Phe Pro Gln Arg Asp Met Pro Phe Gln Ala Leu Leu Leu Tyr Gln
        195                 200                 205

Asp Pro Leu Leu Gly Pro Leu Gln Gly Phe Tyr Pro Val Pro Gln Pro
    210                 215                 220

Val Ala Pro Val Tyr Asn Pro Val
225                 230

<210> SEQ ID NO 43
<211> LENGTH: 24
<212> TYPE: DNA
<213> ORGANISM: Artificial Sequence
<220> FEATURE:
<223> OTHER INFORMATION: neo forward primer

<400> SEQUENCE: 43
gcggccgcgc gcgtcaggtg gcac                                          24

<210> SEQ ID NO 44
<211> LENGTH: 29
<212> TYPE: DNA
<213> ORGANISM: Artificial Sequence
<220> FEATURE:
<223> OTHER INFORMATION: neo reverse primer

<400> SEQUENCE: 44
cgatcggacg ctcagtggaa cgaaaactc                                     29

<210> SEQ ID NO 45
<211> LENGTH: 1902
<212> TYPE: DNA
<213> ORGANISM: Artificial Sequence
<220> FEATURE:
<223> OTHER INFORMATION: neo gene sequence

<400> SEQUENCE: 45
gcgcgtcagg tggcactttt cggggaaatg tgcgcggaac ccctatttgt ttatttttct    60
aaatacattc aaatatgtat ccgctcatga caataaccc tgataaatg cttcaataat    120 attgaaaaag gaagagtcct gaggcggaaa gaaccagctg tggaatgtgt gtcagttagg    180
gtgtggaaag tccccaggct ccccagcagg cagaagtatg caaagcatgc atctcaatta    240
gtcagcaacc aggtgtggaa agtccccagg ctccccagca ggcagaagta tgcaaagcat    300
gcatctcaat tagtcagcaa ccatagtccc gcccctaact ccgcccatcc cgcccctaac    360
tccgcccagt tccgcccatt ctccgcccca tggctgacta atttttttta tttatgcaga    420
ggccgaggcc gcctcggcct ctgagctatt ccagaagtag tgaggaggct ttttggagg    480 cctaggcttt tgcaaagatc gatcaagaga caggatgagg atcgtttcgc atgattgaac    540
aagatggatt gcacgcaggt tctccggccg cttgggtgga gaggctattc ggctatgact    600
gggcacaaca gacaatcggc tgctctgatg ccgccgtgtt ccggctgtca gcgcaggggc    660
gcccggttct ttttgtcaag accgacctgt ccggtgccct gaatgaactg caagacgagg    720
cagcgcggct atcgtggctg gccacgacgg gcgttccttg cgcagctgtg ctcgacgttg    780
tcactgaagc gggaagggac tggctgctat tgggcgaagt gccggggcag gatctcctgt    840
catctcacct tgctcctgcc gagaaagtat ccatcatggc tgatgcaatg cggcggctgc    900
atacgcttga tccggctacc tgcccattcg accaccaagc gaaacatcgc atcgagcgag    960
```

```
cacgtactcg gatggaagcc ggtcttgtcg atcaggatga tctggacgaa gagcatcagg    1020
ggctcgcgcc agccgaactg ttcgccaggc tcaaggcgag catgcccgac ggcgaggatc    1080
tcgtcgtgac ccatggcgat gcctgcttgc cgaatatcat ggtggaaaat ggccgctttt    1140
ctggattcat cgactgtggc cggctgggtg tggcggaccg ctatcaggac atagcgttgg    1200
ctacccgtga tattgctgaa gagcttggcg gcgaatgggc tgaccgcttc ctcgtgcttt    1260
acggtatcgc cgctcccgat tcgcagcgca tcgccttcta tcgccttctt gacgagttct    1320
tctgagcggg actctggggt tcgaaatgac cgaccaagcg acgcccaacc tgccatcacg    1380
agatttcgat tccaccgccg ccttctatga aggttgggc ttcggaatcg ttttccggga     1440
cgccggctgg atgatcctcc agcgcgggga tctcatgctg gagttcttcg cccacccctag   1500 ggggaggcta actgaaacac ggaaggagac aataccggaa ggaacccgcg ctatgacggc    1560
aataaaaaga cagaataaaa cgcacggtgt tgggtcgttt gttcataaac gcggggttcg    1620
gtcccagggc tggcactctg tcgataccc accgagaccc cattgggcc aatacgcccg      1680 cgtttcttcc ttttccccac cccaccccc aagttcgggt gaaggcccag ggctcgcagc     1740
caacgtcggg gcggcaggcc ctgccatagc ctcaggttac tcatatatac tttagattga    1800
tttaaaactt cattttaat ttaaaaggat ctaggtgaag atccttttg ataatctcat       1860 gaccaaaatc ccttaacgtg agttttcgtt ccactgagcg tc                       1902
```

<210> SEQ ID NO 46
<211> LENGTH: 27
<212> TYPE: DNA
<213> ORGANISM: Artificial Sequence
<220> FEATURE:
<223> OTHER INFORMATION: pig beta casein promoter 5.3kb forward primer

<400> SEQUENCE: 46
ggatccgcta tgcaatctca tggaaag                                         27

<210> SEQ ID NO 47
<211> LENGTH: 27
<212> TYPE: DNA
<213> ORGANISM: Artificial Sequence
<220> FEATURE:
<223> OTHER INFORMATION: pig beta casein promoter 5.3kb reverse primer

<400> SEQUENCE: 47
ctcgagtgac cagggtcaac atctact                                         27

<210> SEQ ID NO 48
<211> LENGTH: 29
<212> TYPE: DNA
<213> ORGANISM: Artificial Sequence
<220> FEATURE:
<223> OTHER INFORMATION: pig beta casein 3' arm 5.0kb forward primer

<400> SEQUENCE: 48
ctcgagctgc acttcattct cctggataa                                       29

<210> SEQ ID NO 49
<211> LENGTH: 31
<212> TYPE: DNA
<213> ORGANISM: Artificial Sequence
<220> FEATURE:
<223> OTHER INFORMATION: pig beta casein 3' arm 5.0kb reverse primer

<400> SEQUENCE: 49
gcggccgctt acagtaagac cttcaggagc a                                    31

<210> SEQ ID NO 50
<211> LENGTH: 27
<212> TYPE: DNA
<213> ORGANISM: Artificial Sequence
<220> FEATURE:
<223> OTHER INFORMATION: forward primer for first point mutation

<400> SEQUENCE: 50
acagccacgc agggtcctat ctgcatg                                        27

<210> SEQ ID NO 51
<211> LENGTH: 27
<212> TYPE: DNA
<213> ORGANISM: Artificial Sequence
<220> FEATURE:
<223> OTHER INFORMATION: reverse primer for first point mutation

<400> SEQUENCE: 51
catgcagata ggaccctgcg tggctgt                                        27

<210> SEQ ID NO 52
<211> LENGTH: 31
<212> TYPE: DNA
<213> ORGANISM: Artificial Sequence
<220> FEATURE:
<223> OTHER INFORMATION: forward primer for second point mutation

<400> SEQUENCE: 52
ctcagtgggt taagggtcca gcattgctgt g                                   31

<210> SEQ ID NO 53
<211> LENGTH: 31
<212> TYPE: DNA
<213> ORGANISM: Artificial Sequence
<220> FEATURE:
<223> OTHER INFORMATION: reverse primer for second point mutation

<400> SEQUENCE: 53
cacagcaatg ctggacccett aacccactga g                                  31

<210> SEQ ID NO 54
<211> LENGTH: 29
<212> TYPE: DNA
<213> ORGANISM: Artificial Sequence
<220> FEATURE:
<223> OTHER INFORMATION: forward primer for first point mutation

<400> SEQUENCE: 54
ggacaagagt gtgggtccac tgtgggaag                                      29

<210> SEQ ID NO 55
<211> LENGTH: 29
<212> TYPE: DNA
<213> ORGANISM: Artificial Sequence
<220> FEATURE:
<223> OTHER INFORMATION: reverse primer for first point mutation

<400> SEQUENCE: 55
cttcccacag tggacccaca ctcttgtcc                                      29

<210> SEQ ID NO 56
<211> LENGTH: 24
<212> TYPE: DNA
<213> ORGANISM: Artificial Sequence
<220> FEATURE:
<223> OTHER INFORMATION: forward primer for hEPO

```
<400> SEQUENCE: 56
ggatcctgtg gtcacccggc gcgc                                              24

<210> SEQ ID NO 57
<211> LENGTH: 26
<212> TYPE: DNA
<213> ORGANISM: Artificial Sequence
<220> FEATURE:
<223> OTHER INFORMATION: reverse primer for hEPO

<400> SEQUENCE: 57
gatatcccat gggacaggct ggcgct                                            26

<210> SEQ ID NO 58
<211> LENGTH: 28
<212> TYPE: DNA
<213> ORGANISM: Artificial Sequence
<220> FEATURE:
<223> OTHER INFORMATION: forward primer for WPRE

<400> SEQUENCE: 58
gatatctctg ttcctgttaa tcaacctc                                          28

<210> SEQ ID NO 59
<211> LENGTH: 26
<212> TYPE: DNA
<213> ORGANISM: Artificial Sequence
<220> FEATURE:
<223> OTHER INFORMATION: reverse primer for WPRE

<400> SEQUENCE: 59
gcggccgcga gcccgaggcg aaacag                                            26

<210> SEQ ID NO 60
<211> LENGTH: 2331
<212> TYPE: DNA
<213> ORGANISM: Homo sapiens
<220> FEATURE:
<221> NAME/KEY: gene
<222> LOCATION: (1)..(2331)
<223> OTHER INFORMATION: sequence of hEPO

<400> SEQUENCE: 60
tgtggtcacc cggcgcgccc caggtcgctg agggaccccg gccaggcgcg gagatggggg        60
tgcacggtga gtactcgcgg gctgggcgct cccgcccgcc cgggtccctg tttgagcggg       120
gatttagcgc cccggctatt ggccaggagg tggctgggtt caaggaccgg cgacttgtca       180
aggaccccgg aaggggagg ggggtggggc agcctccacg tgccagcggg acttggggg        240 agtccttggg gatggcaaaa acctgacctg tgaagggac acagtttggg ggttgagggg       300
aagaaggttt ggggggttct gctgtgccag tggagaggaa gctgataagc tgataacctg       360
ggcgctggag ccaccactta tctgccagag ggaagcctc tgtcacacca ggattgaagt       420
ttggccggag aagtggatgc tggtagcctg ggggtgggt gtgcacacgg cagcaggatt       480
gaatgaaggc cagggaggca gcacctgagt gcttgcatgg ttggggacag aaggacgag       540 ctggggcaga gacgtgggga tgaaggaagc tgtccttcca cagccaccct tctccctccc       600
cgcctgactc tcagcctggc tatctgttct agaatgtcct gctgctgt ggcttctcct        660 gtccctgctg tcgctccctc tgggcctccc agtcctgggc gccccaccac gcctcatctg       720
tgacagccga gtcctggaga ggtacctctt ggaggccaag gaggccgaga atatcacggt       780 gagaccccctt ccccagcaca ttccacagaa ctcacgctca gggcttcagg gaactcctcc      840
```

-continued

```
cagatccagg aacctggcac ttggtttggg gtggagttgg aagctagac actgccccc      900
tacataagaa taagtctggt ggccccaaac catacctgga aactaggcaa ggagcaaagc    960
cagcagatcc tacgcctgtg gccagggcca gagccttcag ggacccttga ctccccgggc   1020
tgtgtgcatt tcagacgggc tgtgctgaac actgcagctt gaatgagaat atcactgtcc   1080
cagacaccaa agttaatttc tatgcctgga agaggatgga ggtgagttcc tttttttttt   1140
tttttccttt cttttggaga atctcatttg cgagcctgat tttggatgaa agggagaatg   1200
atcgagggaa aggtaaaatg gagcagcaga gatgaggctg cctgggcgca gaggctcacg   1260
tctataatcc caggctgaga tggccgagat gggagaattg cttgagccct ggagtttcag   1320
accaacctag gcagcatagt gagatccccc atctctacaa acatttaaaa aaattagtca   1380
ggtgaagtgg tgcatggtgg tagtcccaga tatttggaag gctgaggcgg gaggatcgct   1440
tgagcccagg aatttgaggc tgcagtgagc tgtgatcaca ccactgcact ccagcctcag   1500
tgacagagtg aggccctgtc tcaaaaaaga aagaaaaaa gaaaataat gagggctgta    1560
tggaatacgt tcattattca ttcactcact cactcactca ttcattcatt cattcattca   1620
acaagtctta ttgcatacct tctgtttgct cagcttggtg cttggggctg ctgaggggca   1680
ggagggagag ggtgacatgg gtcagctgac tcccagagtc cactccctgt aggtcgggca   1740
gcaggccgta gaagtctggc agggcctggc cctgctgtcg gaagctgtcc tgcggggcca   1800
ggccctgttg gtcaactctt cccagccgtg ggagcccctg cagctgcatg tggataaagc   1860
cgtcagtggc cttcgcagcc tcaccactct gcttcgggct ctgggagccc aggtgagtag   1920
gagcggacac ttctgcttgc cctttctgta agaaggggag aagggtcttg ctaaggagta   1980
caggaactgt ccgtattcct tcccttcg tggcactgca gcgacctcct gttttctcct    2040
tggcagaagg aagccatctc ccctccagat gcggcctcag ctgctccact ccgaacaatc   2100
actgctgaca ctttccgcaa actcttccga gtctactcca atttcctccg gggaaagctg   2160
aagctgtaca caggggaggc ctgcaggaca ggggacagat gaccaggtgt gtccacctgg   2220
gcatatccac cacctccctc accaacattg cttgtgccac ccctccccc gccactcctg    2280
aaccccgtcg agggctctc agctcagcgc cagcctgtcc catggctcga g              2331
```

<210> SEQ ID NO 61
<211> LENGTH: 619
<212> TYPE: DNA
<213> ORGANISM: Woodchuck hepatitis B virus
<220> FEATURE:
<221> NAME/KEY: misc_signal
<222> LOCATION: (1)..(619)
<223> OTHER INFORMATION: sequence of WPRE

<400> SEQUENCE: 61

```
tctgttcctg ttaatcaacc tctggattac aaaatttgtg aaagattgac tggtattctt     60
aactatgttg ctccttttac gctatgtgga tacgctgctt taatgccttt gtatcatgct    120
attgcttccc gtatggcttt catttctcc tccttgtata atcctggtt gctgtctctt      180
tatgaggagt tgtggcccgt tgtcaggcaa cgtggcgtgg tgtgcactgt gtttgctgac    240
gcaacccca ctggtgggg cattgccacc acctgtcagc tcctttccgg gactttcgct     300
ttcccctcc ctattgccac ggcggaactc atcgccgcct gccttgcccg ctgctggaca    360
ggggctcggc tgttgggcac tgacaattcc gtggtgttgt cggggaagct gacgtccttt    420
ccatggctgc tcgcctgtgt tgccacctgg attctgcgcg gacgtccttt ctgctacgtc    480
ccttcggccc tcaatccagc ggaccttcct tcccgcggcc tgctgccggc tctgcggcct    540
```

```
cttccgcgtc ttcgccttcg ccctcagacg agtcggatct ccctttgggc cgcctccccg    600
cctgtttcgc ctcgggctc                                                 619
```

<210> SEQ ID NO 62
<211> LENGTH: 27
<212> TYPE: DNA
<213> ORGANISM: Artificial Sequence
<220> FEATURE:
<223> OTHER INFORMATION: pig beta casein promoter 5.3kb forward primer

<400> SEQUENCE: 62

```
ggatccgcta tgcaatctca tggaaag                                         27
```

<210> SEQ ID NO 63
<211> LENGTH: 27
<212> TYPE: DNA
<213> ORGANISM: Artificial Sequence
<220> FEATURE:
<223> OTHER INFORMATION: pig beta casein promoter 5.3kb reverse primer

<400> SEQUENCE: 63

```
ggatcctgac cagggtcaac atctact                                         27
```

<210> SEQ ID NO 64
<211> LENGTH: 31
<212> TYPE: DNA
<213> ORGANISM: Artificial Sequence
<220> FEATURE:
<223> OTHER INFORMATION: pig beta casein 3' arm 5.0kb forward primer

<400> SEQUENCE: 64

```
gcggccgcct gcacttcatt ctcctggata a                                    31
```

<210> SEQ ID NO 65
<211> LENGTH: 31
<212> TYPE: DNA
<213> ORGANISM: Artificial Sequence
<220> FEATURE:
<223> OTHER INFORMATION: pig beta casein 3' arm 5.0kb reverse primer

<400> SEQUENCE: 65

```
gcggccgctt acagtaagac cttcaggagc a                                    31
```

<210> SEQ ID NO 66
<211> LENGTH: 35
<212> TYPE: DNA
<213> ORGANISM: Artificial Sequence
<220> FEATURE:
<223> OTHER INFORMATION: first forward primer for beta hEPO

<400> SEQUENCE: 66

```
gacttgatcg ccatgggggt gcacggtgag tactc                                35
```

<210> SEQ ID NO 67
<211> LENGTH: 33
<212> TYPE: DNA
<213> ORGANISM: Artificial Sequence
<220> FEATURE:
<223> OTHER INFORMATION: second forward primer for beta hEPO

<400> SEQUENCE: 67

```
gatatcattc acaggacttg atcgccatgg ggg                                  33
```

<210> SEQ ID NO 68
<211> LENGTH: 26

```
<212> TYPE: DNA
<213> ORGANISM: Artificial Sequence
<220> FEATURE:
<223> OTHER INFORMATION: reverse primer for beta hEPO

<400> SEQUENCE: 68
gaattcatgg gacaggctgg cgctga                                      26

<210> SEQ ID NO 69
<211> LENGTH: 28
<212> TYPE: DNA
<213> ORGANISM: Artificial Sequence
<220> FEATURE:
<223> OTHER INFORMATION: forward primer for promoter

<400> SEQUENCE: 69
gtcgacagtt gtagctgctg acctacac                                    28

<210> SEQ ID NO 70
<211> LENGTH: 30
<212> TYPE: DNA
<213> ORGANISM: Artificial Sequence
<220> FEATURE:
<223> OTHER INFORMATION: reverse primer for promoter

<400> SEQUENCE: 70
gatatcgggg aaatgaggga aaaaatgtat                                  30

<210> SEQ ID NO 71
<211> LENGTH: 31
<212> TYPE: DNA
<213> ORGANISM: Artificial Sequence
<220> FEATURE:
<223> OTHER INFORMATION: forward primer for 3' arm

<400> SEQUENCE: 71
gcggccgcct gcacttcatt ctcctggata a                                31

<210> SEQ ID NO 72
<211> LENGTH: 29
<212> TYPE: DNA
<213> ORGANISM: Artificial Sequence
<220> FEATURE:
<223> OTHER INFORMATION: reverse primer for 3' arm

<400> SEQUENCE: 72
ccgcggttac agtaagacct tcaggagca                                   29
```

GENE OF PORCINE BETA CASEIN, A PROMOTER OF THE SAME AND THE USE THEREOF

RELATED APPLICATIONS

This application is the National Stage of International Application. No. PCT/KR2008/007823, filed 31 Dec. 2008, which claims benefit of priority to KR 10-2008-0062767, filed 30 Jun. 2008, entitled "A GENE OF PORCINE BETA CASEIN, A PROMOTER OF THE SAME AND THE USES THEREOF."

TECHNICAL FIELD

The present invention relates to a porcine beta-casein gene, a porcine beta-casein gene promoter, an expression vector comprising the same, and a method for the production of a target protein using the same.

BACKGROUND ART

As an attempt to achieve maximum production of beneficial proteins (such as EPO with high economic value-added) in the medicinal field, mass production methods using cell culture techniques have been mainly used.

Korean Patent Application No. 94-12082 discloses an expression vector containing a modified recombinant human erythropoietin (rhEPO) gene. Despite feasibility of mass production of EPO in the animal cell line COS-7 (ATCC CRL 1651, African Green Monkey Kidney Cell) transformed with the same expression vector, this technique disadvantageously suffers from a cumbersome need of continuous transformation, which makes it unsuitable for industrial-scale production of a target protein. Further, Korean Patent No. 10-0232640 and Korean Patent Application Publication No. 1999-0075254 also disclose the production of EPO by transgenic cell line culture. However, these cell culture methods still suffer from disadvantages such as high production costs due to use of animal blood as a culture medium, and requirement of expert and sophisticated knowledge in the culture technique.

On the other hand, the production of beneficial proteins using transgenic animals is attracting a great deal of interest due to having advantages such as easy and convenient production, isolation and purification of target proteins and maintenance of superior activity, as compared to conventional cell culture techniques, because the target proteins are contained in body fluids secreted by animals. For example, Korean Patent Application Publication No. 2004-0081456 discloses a transgenic animal for the production of EPO in porcine milk, using a whey acidic milk protein promoter (WAP).

As a result of a variety of extensive and intensive studies and experiments to solve the problems as described above and to develop a mammary gland-specific promoter with high-efficiency expression of a target protein in milk, the inventors of the present invention succeeded in sequencing of a beta-casein gene and a promoter thereof. The present invention has been completed based on this finding.

DISCLOSURE OF THE INVENTION

Technical Problem

The present invention is intended to provide a porcine beta-casein gene and a promoter thereof, and a method for mass production of a target protein using the same.

Technical Solution

The present invention provides a porcine beta-casein gene. The beta-casein gene of the present invention specifically comprises a sequence as set forth in SEQ ID NO: 1, and the sequence of SEQ ID NO: 1 contains a promoter, and a sequence of a 3' untranslated region (UTR).

Further, the present invention provides a promoter of SEQ ID NO: 2 corresponding to a sequence of 1 to 5480 contiguous nucleotides, among the sequence of SEQ ID NO: 1, and the promoter is situated at the 5' side of a structural gene to thereby control expression of the structural gene.

The porcine beta-casein gene or promoter of the present invention may be one selected from functional equivalents thereof having one or more of disruption, deletion, insertion, point, substitution, nonsense, missense, polymorphism and rearrangement mutations in the sequence of SEQ ID NO: 1 or SEQ ID NO: 2.

Further, the present invention provides an expression vector comprising an entire or partial promoter sequence of SEQ ID NO: 2. Preferably, the expression vector of the present invention contains a sequence of SEQ ID NO: 3 or SEQ ID NO: 4. The sequence of SEQ ID NO: 2, SEQ ID NO: 3 or SEQ ID NO: 4 serves as a promoter through the incorporation thereof into the vector and is referred to herein as a promoter sequence or porcine beta-casein gene promoter sequence. As used herein, the term "porcine beta-casein gene promoter" refers to a promoter derived from a porcine beta-casein gene.

SEQ ID NO: 3 and SEQ ID NO: 4 respectively correspond to a sequence consisting of 67-5299 nucleotides and a sequence consisting of 561-5480 nucleotides, among an entire genomic sequence of a porcine beta-casein gene of SEQ ID NO: 1, and contains in common a sequence consisting of 561-5299 nucleotides among the sequence of SEQ ID NO: 1 and an exon 1 region.

If necessary, the expression vector of the present invention may additionally contain regulatory factors at suitable sites or loci thereof. Examples of the regulatory factors may include another promoter, enhancer, selective marker, 5'-untranslated region (UTR), 3'-UTR, polyadenylation signal, ribosome-binding sequence, sequence(s) capable of being inserted into a specific site of a genome, intron and woodchuck hepatitis virus posttranscriptional regulatory element (WPRE). Incorporation of such additional elements into the expression vector will provide various advantages such as easy and convenient construction of a transgenic cell line of interest, and maximized and stable expression of target proteins.

The selective marker is preferably a neomycin-resistant gene or the like. The selective marker may be one excised from a commercially available vector. The neomycin-resistant gene is a gene conferring resistance to G418 which is a reagent used in the construction of a cell line, and it may serve as an efficient selective marker upon the construction of an animal cell line that expresses a target protein under the control of a promoter.

The insulator is a factor that assists in the action of a regulatory factor adjacent to the promoter and facilitates position-independent expression of a protein. The insulator factor allows for stable expression of the protein under the control of a promoter. The insulator may be one excised from a commercially available vector.

WPRE is a regulatory factor that can contribute to the stabilization of mRNA molecules to thereby augment synthesis of proteins. This regulator enables high expression of proteins under the control of a promoter. WPRE may also be a truncated one derived from a commercially available vector.

The expression vector of the present invention may further comprise a sequence as set forth in SEQ ID NO: 5. The sequence of SEQ ID NO: 5 forms a 3' arm of the vector and assists in easy construction of a transgenic cell line, and maximization and stabilization of target protein expression.

SEQ ID NO: 5 corresponds to a sequence ranging from nucleotide 10474 to nucleotide 15485, among an entire genomic sequence of the porcine beta-casein gene of SEQ ID NO: 1 and it contains an exon 9 region.

Positions of sequences of SEQ ID NOs: 3, 4 and 5 among an entire genomic sequence of the porcine beta-casein gene are as shown in FIG. 1.

The vector of the present invention is preferably constructed to contain the sequence of SEQ ID NO: 3 and the sequence of SEQ ID NO: 5.

Specifically, the vector of the present invention has a cleavage map as shown in FIG. 2. The pBC 1-Pig β casein vector was deposited with the Korean Collection for Type Cultures (KCTC), the Korean Research Institute of Bioscience and Biotechnology (KRIBB, Daejon, Korea), under Accession Number KCTC 11327BP. The expression vector pBC1-Pig β casein of the present invention has a pBC1 vector as a basic backbone, to which a neomycin-resistant gene was fused as a selective marker.

The expression vector of the present invention may express a target protein by further incorporation of a target protein-encoding sequence at a 3' side of the promoter sequence.

The target protein is an industrially applicable beneficial protein and may be any protein that is used, for example, as an active ingredient of pharmaceuticals. Examples of the target protein may include EPO (erythropoietin), aldosterone, adrenocorticotropin, blood clotting factors, gonadotropin, insulin, prolactin, and vasopressin. Preferred is hEPO.

The present invention provides a vector having a cleavage map of FIG. 3, as a preferable example of an expression vector harboring a neomycin-resistant gene, an insulator, WPRE, and the like. Specifically, the pBC1-Pig β casein+ hEPO-WPRE vector was deposited with the Korean Collection for Type Cultures (KCTC), the Korean Research Institute of Bioscience and Biotechnology (KRIBB, Daejon, Korea), under Accession Number KCTC 11328BP.

The expression vector pBC1-Pig β casein+hEPO-WPRE has a pBC1 vector as a basic backbone, wherein an hEPO-encoding gene is fused to a 3' side of the promoter region of the present invention, and WPRE is fused to a 3' side of the hEPO gene The expression vector of the present invention may be constructed in the form of a knock-in vector.

In the context of the present invention, the knock-in vector is a vector capable of inserting a target gene into a specific site or locus of a genome, and it contains a sequence homologous to a particular gene to be targeted, so as to result in homologous recombination therebetween. The knock-in vector of the present invention is a beta-casein targeting vector where a target protein-encoding nucleic acid sequence is inserted into a beta-casein gene present on the genome.

The knock-in vector of the present invention is preferably constructed to contain a sequence of SEQ ID NO: 4 and a sequence of SEQ ID NO: 5.

The knock-in vector may be constructed to select transgenic cells using a positive and/or negative selective marker, if necessary. The selective marker is intended to select vector-transformed cells and may employ genes capable of conferring selectable phenotypes, such as drug resistance, nutritional auxotrophy, resistance to cytotoxic agents, and expression of surface proteins. The selective marker may be broadly classified into a positive selective marker and a negative selective marker.

As used herein, the term "positive selective marker" refers to a gene that makes cells expressing the positive selective marker to survive against a selective agent, so that it is capable of conferring positive selective characteristics for the cells expressing that marker. Examples of the positive selective marker may include neomycin (Neo)-resistant gene, hygromycin (Hyg)-resistant gene, etc.

The term "negative selective marker" refers to a gene which removes cells with random-integration, so that it is capable of conferring negative selection characteristics for the cells expressing that marker. Examples of the negative selective marker may include Herpes simplex virus-thymidine kinase (HSV-tk) gene, hypoxanthine phosphoribosyl transferase (Hprt) gene, cytosine deaminase gene, Diphtheria toxin gene, etc. The negative selective marker is positioned at the 5' terminus of the promoter region or at the 3' terminus of the 3' arm.

The positive selective marker and the negative selective marker may have independent promoters, poly(A), and the like. Examples of the promoter that can be used in the present invention may include simian virus 40 (SV40), mouse mammary tumor virus (MMTV) promoter, HIV long terminal repeat (LTR) promoter, Moloney virus, Cytomegalovirus (CMV) promoter, Epstein-Barr virus (EBV) promoter, Rous sarcoma virus (RSV) promoter, phosphoglycerate kinase (PGK) promoter, etc.

When homologous recombination takes place between the knock-in vector of the present invention and the beta-casein gene on the genome, a target protein-encoding nucleic acid on the vector is integrated into the beta-casein genomic gene of the host cell and is then expressed instead of the beta-casein protein of the host cell.

The present invention provides a vector having a cleavage map of FIG. 4, as a preferable example of a knock-in vector employing a neomycin-resistant gene as a positive selective marker and Herpes simplex virus-thymidine kinase (HSV-tk) as a negative selective marker.

Specifically, the Pig β casein–hEPO knock-in vector was deposited with the Korean Collection for Type Cultures (KCTC), the Korean Research Institute of Bioscience and Biotechnology (KRIBB, Daejon, Korea), under Accession Number KCTC 11329BP.

The Pig β casein–hEPO knock-in vector has a Lox A vector as a basic backbone, wherein hEPO is fused to a 3' side of the promoter (referring to the Pig β casein 5' arm region of FIG. 4), a neomycin-resistant gene as a positive selective marker is fused to a 3' side of hEPO, a 3' arm (referring to the Pig β casein 3' arm of FIG. 4) is fused to a 3' side of the neomycin-resistant gene, and a Herpes simplex virus-thymidine kinase (HSV-tk) gene is fused to a 3' side of the 3' arm.

The vector of the present invention may be constructed by any conventional gene recombination technique well-known in the art. Site-specific DNA cleavage and splicing may be carried out using conventional enzymes known in the art.

Further, the present invention provides an animal somatic cell transformed by introduction of the expression vector of the present invention.

The animal somatic cell to which the vector of the present invention will be introduced may be a primary, secondary or permanent cell derived from suitable animals including pigs.

Intracellular introduction of the vector of the present invention may be carried out by any conventional intracellular introduction method of nucleic acids, that is, techniques known in the art, such as electroporation, calcium phosphate co-precipitation, retroviral infection, microinjection, DEAE-dextran facilitated transfection, cationic liposome-mediated transfection, etc. When it is desired to perform intracellular introduction of a vector, the vector may be introduced in the form of a linearized vector or in the form of a plasmid-free linearized vector, by digestion of a circular vector with suitable restriction enzymes.

The promoter gene of the present invention specifically expresses a target protein only in mammary gland tissues. Casein accounts for 90% of protein components in porcine milk and is broadly categorized into alpha-, beta- and gamma-casein. Since beta-casein contributes to a considerable portion of protein components, amounting to 27%, the vector employing the porcine beta-casein promoter may be constructed to exhibit mammary gland-specific expression of exogenous target proteins in lactating animals, particularly pigs.

Further, the present invention provides an animal embryo constructed by nuclear transfer of a nucleus of an animal somatic cell transformed with the expression vector of the present invention into an enucleated egg.

As used herein, the term "nuclear transfer" refers to implantation of a cell nucleus into an enucleated egg. The offspring produced by implantation of the nuclear-transferred fertilized egg (or embryo) are genetically completely identical clones because genetic materials of a nuclear donor cell were thoroughly and intactly transferred into a nuclear recipient cytoplasm.

Further, the present invention provides a transgenic animal obtained by implantation of an animal embryo of the present invention.

Examples of the animals that can be transformed with the expression vector of the present invention may include all kinds of lactating animals including pig, mouse, cow, sheep, and goat.

Production of a transgenic animal using the expression vector of the present invention is carried out by a conventional method known in the art.

For example, when an animal to be transformed is a mouse, embryos (or fertilized eggs) are collected from a healthy individual, and the expression vector of the present invention is introduced into the embryos. Thereafter, a pseudopregnant mouse is obtained using a vasoligated mouse, the embryos are implanted into an oviduct of the pseudopregnant mouse as a surrogate mother (or recipient), and transgenic mice are then selected from among the offspring obtained from the surrogate mother.

When an animal to be transformed is a pig, porcine follicular oocytes are collected from a healthy animal and cultured in an in vitro maturation (IVM) medium. Further, the expression vector of the present invention is introduced into donor somatic cells collected and cultured from the porcine fetus, and somatic cells with integration of the vector are selected and cultured. The in vitro matured eggs are enucleated, the donor cells are injected into the enucleated space of the egg cells from which nuclei were removed, and the donor cells and the cytoplasm of the nuclear-transferred eggs are fused by an electrofusion technique, followed by in vitro culture of the fusion. The resulting cloned embryos are implanted into the recipient pigs which were subjected to superovulation treatment, and the transgenic pigs are then selected from among the offspring obtained from the recipient pigs.

Thereafter, milk is collected from the individual where correct transformation was confirmed, and a target protein is isolated and purified therefrom to produce a final protein (A. Gokana, J. J. Winchenn, A. Ben-Ghanem, A. Ahaded, J. P. Cartron, P. Lambin (1997) Chromatographic separation of recombinant human erythropoietin isoforms, Journal of Chromatography, 791, 109-118).

In the production of the target protein of the present invention, isolation and purification of the protein may be carried out by a conventional method known in the art, for example filtration or chromatography.

The thus-constructed transgenic animal of the present invention can express the target protein in milk.

Therefore, the porcine beta-casein gene of the present invention, the promoter thereof, and the expression vector and transgenic animal using the same can be beneficially used for the production of target proteins.

Details relating to genetic engineering techniques in the present invention can be found in the following literature: Sambrook, et al. Molecular Cloning, A Laboratory Manual, Cold Spring Harbor Laboratory Press, Cold Spring Harbor, N.Y. (2001); and Frederick M. Ausubel et al., Current Protocols in Molecular Biology volume 1, 2, 3, John Wiley & Sons, Inc. (1994).

Advantageous Effects

A porcine beta-casein gene promoter facilitates mammary gland-specific expression of a target protein. Therefore, a promoter of the present invention and an animal transformed with an expression vector constructed using the same promoter enable high-concentration secretion of the target protein in milk, which consequently will provide benefits for the production of useful proteins that are medically and pharmaceutically valuable.

MODE FOR INVENTION

Figure 1:
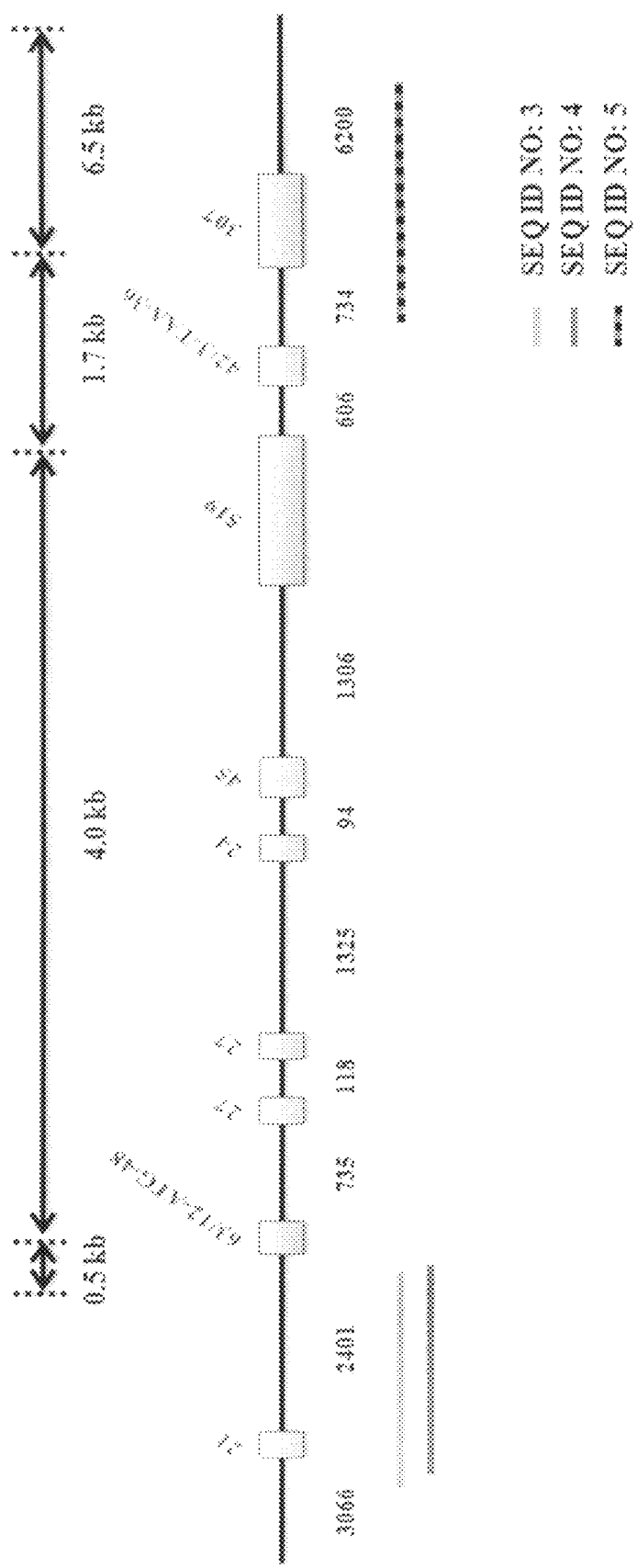
FIG. 1 shows positions of sequences found by PCR amplification during sequencing of a porcine beta-casein in accordance with the present invention, as depicted in an entire sequence of porcine beta-casein.

Now, the present invention will be described in more detail with reference to the following Examples. These examples are provided only for illustrating the present invention and should not be construed as limiting the scope and spirit of the present invention.

Example 1

Isolation and Cloning of Porcine Beta-Casein Gene

In order to construct a mammary gland-specific vector of the present invention, a porcine beta-casein gene was sequenced using bacterial artificial chromosome (BAC) clones provided by The National Livestock Research Institute (Korea).

1) Sequencing of Porcine Beta-Casein Using BAC Clones

For sequencing of a porcine beta-casein gene, a primer pair consisting of 5'-TCTTGAAAACCTACCAAGTGC-3' (forward, SEQ ID NO: 6) and 5'-ATTCGTACAACACGGT-CATTT-3' (reverse, SEQ ID NO: 7) was constructed with reference to a sequence of a porcine beta-casein promoter region (5.5 kb) available from The National Center for Biotechnology Information (NCBI) (http://www.ncbi.nlm.nih.gov, AY452035). The sequence of SEQ ID NO: 6 corresponds to a sequence of 2719 to 2739 nucleotides among the sequence of SEQ ID NO: 1, and the sequence of SEQ ID NO: 7 corresponds to a sequence of 3284 to 3304 nucleotides among the sequence of SEQ ID NO: 1. Using this primer set, four clones (155F1, 188A9, 616B6, and 874E5) were obtained by PCR amplification from The National Livestock Research Institute (Korea). PCR was carried out as follows: one cycle of denaturation at 94° C. for 5 minutes; and 35 cycles of denaturation at 94° C. for 30 seconds, primer annealing at 56° C. for 30 seconds and elongation at 72° C. for 30 seconds.

In order to screen a porcine beta-casein gene using four clones thus obtained, primer sequences (SEQ ID NO: 8 to SEQ ID NO: 13) for use in PCR amplification of the porcine beta-casein were constructed with reference to portions that are highly homologous and well conserved among different species, obtained by comparing beta-casein cDNA sequences of human, cow, horse and mouse whose beta-casein sequences were already known.

TABLE 1

| Names | Primers | SEQ ID NO |
|---|---|---|
| ATG up forward | 5'-AGAGAACTCTATCCAATCACTT-3' | 8 |
| ATG up reverse | 5'-GCAAGGATGAGGAGCTTCAT-3' | 9 |
| ATG down forward | 5'-ATGAAGCTCCTCATCCTTGC-3' | 10 |
| ATG down reverse | 5'-TCTGCTGGAGATTTAGGGAAG-3' | 11 |
| 3' down forward | 5'-CTTCCCTAAATCTCCAGCAGA-3' | 12 |
| 3' down reverse | 5'-GTTGTCACATTTCCAGTCACA-3' | 13 |

PCR amplification was carried out using the constructed primers and 616B6 out of four BAC clones as a template. The resulting PCR products of 0.5 kb (SEQ ID NO: 14), 4.0 kb (SEQ ID NO: 15) and 1.7 kb (SEQ ID NO: 16) were each cloned into a pGEM-T vector, followed by continuous sequencing.

TABLE 2

| | Primers for sequencing | SEQ ID NO |
|---|---|---|
| For 4.0 kb | 5'-CCTGTGTCTATTGAACAGAGA-3' | 17 |
| | 5'-AGAAGGAAGAACTCAATGCAT-3' | 18 |
| | 5'-AATGGTACATCACTAAACTTTG-3' | 19 |
| | 5'-GGTGTGATCTGTTTTCTAGGA-3' | 20 |
| | 5'-GTGTGACAACTTGCATAGTTAT-3' | 21 |
| For 1.7 kb | 5'-GTCCAAGTTTATTCACTGTGC-3' | 22 |

Positional structures of PCR-screened sequences are as shown in FIG. 1.

After specific primers were constructed using the analyzed sequences, a 6.5-kb fragment (SEQ ID NO: 31) at a 3' side of the porcine beta-casein was sequenced by repetitive sequencing (SEQ ID NO: 23 to SEQ ID NO: 30) using the BAC clone 616B6 as a template.

TABLE 3

| SEQ ID NO | Primers for sequencing |
|---|---|
| 23 | 5'-TGGTGCTGTATAAGTTAGGCT-3' |
| 24 | 5'-TAAGTCCTTGACATTGCTGAG-3' |
| 25 | 5'-CTTTGCATCGTCTCTTCTGG-3' |
| 26 | 5'-ACCCAATACTCCTAACAATGC-3' |
| 27 | 5'-CCTCAGAAACTGTAATAGTTG-3' |
| 28 | 5'-CCTTTCTGCTGTATCCTCAC-3' |
| 29 | 5'-CAGGATGTCGCTTGAACAAG-3' |
| 30 | 5'-GGAGACTAGTGTCACCAAAC-3' |

2) Sequencing of Beta-Casein from Berkshire Pigs

Based on a DNA sequence of the porcine beta-casein obtained from Bac clones, a sequence of beta-casein was sequenced from a genomic DNA of Berkshire pigs. The searched beta-casein 12.6-kb fragment and the already-sequenced 5.5-kb fragment were ligated and the resulting 17.7-kb sequence fragment was divided into five parts (3.6 kb, 3.9 kb, 4.2 kb, 3.3 kb, 3.8 kb) which correspond to primer sequences (SEQ ID NO: 32 to SEQ ID NO: 41) for use in PCR amplification (PT-200, BIO-RAD). PCR was carried out as follows: one cycle of denaturation at 94° C. for 5 minutes; and 35 cycles of denaturation at 94° C. for 30 seconds, primer annealing at 56° C. for 30 seconds and elongation at 72° C. for 4 minutes.

The resulting PCR products were each cloned into a pGEM-T vector, followed by sequencing. Analysis of sequences was conducted by Sogent (Korea) using a Bioedit program.

TABLE 4

| Primers | | SEQ ID NO |
|---|---|---|
| Forward 3.6 kb | 5'-ATCAGATGTTATTTTATGTGGCTAATC-3' | 32 |
| Reverse 3.6 kb | 5'-ATTTTTAGAAGAAGAGCATATTTGTCA-3' | 33 |
| Forward 3.9 kb | 5'-AGGGTATTTGTGGGTATTTAAGATAGT-3' | 34 |
| Reverse 3.9 kb | 5'-AATGGTACATCACTAAACTTTGACTCT-3' | 35 |
| Forward 4.2 kb | 5'-TCTCTCTCTATATTAACCTCATTCACTG-3' | 36 |
| Reverse 4.2 kb | 5'-CCTTTTGTGATCATGATATAGTAAACA-3' | 37 |
| Forward 3.3 kb | 5'-CAGTTGCCTATACACTTACACTTGAT-3' | 38 |
| Reverse 3.3 kb | 5'-AGTCATGGTCTAAAGTGGAATGGGA-3' | 39 |
| Forward 3.8 kb | 5'-AACTAACATTTCTTCTCTTAGGTATAC-3' | 40 |
| Reverse 3.8 kb | 5'-AAAGGATTATATGCTATCTAATATAGAGT-3' | 41 |

As a result, the porcine beta-casein genomic DNA sequence (SEQ ID NO: 1) of the Berkshire pig and sequence information thereof were successfully acquired.

The sequence of SEQ ID NO: 1 is an entire genomic sequence of the porcine beta-casein gene and has a length of 17660 bp. In the sequence of SEQ ID NO: 1, the structural gene region is a sequence ranging from nucleotide 3067 to nucleotide 11460, the initiation codon is a sequence ranging from nucleotide 5501 to nucleotide 5503, and the termination codon is a sequence ranging from nucleotide 10381 to nucleotide 10383. In addition, the 5' UTR region is a sequence ranging from nucleotide 3067 to nucleotide 3087 and from nucleotide 5489 to nucleotide 5500, the 3' UTR region is a sequence ranging from nucleotide 10384 to nucleotide 10419 and from nucleotide 11154 to nucleotide 11460, and the poly(A) signal region is a sequence ranging from nucleotide 11440 to nucleotide 11445. The exon region is a sequence ranging from nucleotide 3074 to nucleotide 3087, from nucleotide 5489 to nucleotide 5551, from nucleotide 6287 to nucleotide 6313, from nucleotide 6432 to nucleotide 6458, from nucleotide 7784 to nucleotide 7807, from nucleotide 7902 to nucleotide 7946, from nucleotide 9253 to nucleotide 9771, from nucleotide 10378 to nucleotide 10419, and from nucleotide 11154 to nucleotide 11460. The intron region is a sequence ranging from nucleotide 3088 to nucleotide 5488, from nucleotide 5552 to nucleotide 6286, from nucleotide 6314 to nucleotide 6431, from nucleotide 6459 to nucleotide 7783, from nucleotide 7808 to nucleotide 7901, from nucleotide 7947 to nucleotide 9252, from nucleotide 9772 to nucleotide 10377, and from nucleotide 10420 to nucleotide 11153. The CDS (coding sequence) is a sequence ranging from nucleotide 5501 to nucleotide 5551, from nucleotide 6287 to nucleotide 6313, from nucleotide 6432 to nucleotide 6458, from nucleotide 7784 to nucleotide 7807, from nucleotide 7902 to nucleotide 7946, from nucleotide 9253 to nucleotide 9771, and from nucleotide 10378 to nucleotide 10383.

In addition, a beta-casein amino acid sequence (SEQ ID NO: 42) was analyzed.

The analyzed porcine beta-casein sequence and information thereof were registered in NCBI (EU025876).

Example 2

Construction of pBC1-Pig β Casein Cloning Vector

A cloning vector was constructed by respectively replacing a goat beta-casein promoter region and a 3' genomic DNA region with the promoter sequence and the 3' arm sequence in a vector having substitution of an ampicillin-resistant gene of a pBC1 vector (Invitrogen, USA) with a neomycin-resistant gene {A "neo" gene capable of conferring drug resistance to G418 was obtained from a pEGFP-N1 vector (Clontech, USA) by amplification of a 1.9-kb PCR product (SEQ ID NO: 45) using a forward primer 5'-GCGGCCGCGCGCGTCAG-GTGGCAC-3' (SEQ ID NO: 43) and a reverse primer 5'-CGATCGGACGCTCAGTGGAACGAAAACTC-3' (SEQ ID NO: 44), and was then cloned into a pGEM T-easy vector. The 1.9-kb neo gene cloned into the T-vector was digested with restriction endonucleases NotI and PvuI to prepare an insert. In addition, an amp gene (ampicillin-resistance gene) region of the pBC1 vector was removed by NotI and PvuI cleavage to prepare a vector. The resulting insert fragment and vector part were ligated to construct a pBC1 vector into which the neo gene (neomycin-resistance gene) was inserted}.

The promoter sequence 5.3 kb (SEQ ID NO: 3) and the 3' arm sequence 5.0 kb (SEQ ID NO: 5) were subjected to PCR amplification (PT-200, BIO-RAD) using primer sequences (SEQ ID NO: 46 to SEQ ID NO: 49). PCR was carried out as follows: one cycle of denaturation at 94° C. for 5 minutes; and 35 cycles of denaturation at 94° C. for 30 seconds, primer annealing at 56° C. for 30 seconds and elongation at 72° C. for 5 minutes. Each of the resulting PCR products was cloned into a pGEM-T vector (Promega, USA).

TABLE 5

| Primers | | SEQ ID NO |
|---|---|---|
| Forward primer for promoter amplification | 5'-GGATCCGCTATGCAATCTCATG GAAAG-3' | 46 |
| Reverse primer for promoter amplification | 5'-CTCGAGTGACCAGGGTCAACAT CTACT-3' | 47 |
| Forward primer for 3' arm amplification | 5'-CTCGAGCTGCACTTCATTCTCC TGGATAA-3' | 48 |
| Reverse primer for 3' arm amplification | 5'-GCGGCCGCTTACAGTAAGACCT TCAGGAGCA-3' | 49 |

In order to avoid possible BamHI digestion, two BamHI sites (GGATCC) present in the porcine beta-casein promoter sequence were subjected to repetitive point mutations as follows. For introduction of point mutations, one of two restriction sites was first selected and the corresponding primer was constructed. The pGEM-T vector DNA containing a porcine beta-casein 5' promoter region was purified and then subjected to PCR amplification using 20 ng of template DNA and a pair of point mutation primers. PCR was carried out as follows: one cycle of denaturation at 95° C. for 30 seconds; and 15 cycles of denaturation at 95° C. for 30 seconds, primer annealing at 55° C. for 1 minute and elongation at 72° C. for 8.5 minutes. In order to eliminate the template (with no introduction of point mutation) DNA, 1 µl of Mutazyme™ was added thereto, followed by reaction at 37° C. for 1 hour. 10 µl of the reaction product was transformed into DH10B competent cells (Invitrogen, USA) which were then plated on an LB+Ampicillin solid medium and cultured at 37° C. for 20 hours. Colonies grown on the LB+Ampicillin solid medium were cultured on an LB+Ampicillin liquid medium, followed by DNA purification and sequencing to confirm whether BamHI sites underwent point mutations (GGATCC->GGACCC). Using DNA of colonies having the point mutation at one restriction site, the other BamHI site was also made to have a point mutation according to the same method. The point mutation method used herein was carried out using a Site-Directed Mutagenesis kit (iNtRON).

Primer sequences used in the point mutation of the promoter sequence are as follows.

TABLE 6

| Primers | | SEQ ID NO |
|---|---|---|
| Forward primer for primary point mutation | 5'-ACAGCCACGCAGGGTCCTATCT GCATG-3' | 50 |
| Reverse primer for primary point mutation | 5'-CATGCAGATAGGACCCTGCGTG GCTGT-3' | 51 |
| Forward primer for secondary point mutation | 5'-CTCAGTGGGTTAAGGGTCCAGC ATTGCTGTG-3' | 52 |
| Reverse primer for secondary point mutation | 5'-CACAGCAATGCTGGACCCTTAA CCCACTGAG-3' | 53 |

The 3' arm sequence also has one BamHI site which was therefore point-mutated in the same manner as in point mutation of the promoter region.

Primer sequences used for the point mutation of the 3' arm sequence are as follows:

TABLE 7

| Primers | | SEQ ID NO |
|---|---|---|
| Forward primer for primary point mutation | 5'-GGACAAGAGTGTGGGTCCACTG TGGGAAG-3' | 54 |
| Reverse primer for primary point mutation | 5'-CTTCCCACAGTGGACCCACACT CTTGTCC-3' | 55 |

The porcine beta-casein promoter sequence present in the pGEM-T vector was digested with BamHI and XhoI to prepare an 8.3-kb vector. In addition, the 3' arm sequence was digested with XhoI and NotI to prepare a 5.0-kb insert (SEQ ID NO: 5). The resulting two restriction fragments were ligated to clone a pGEM-T-Pig β casein 5'+3' vector.

The pBC1 vector was digested with BamHI and NotI to prepare a 10-kb vector, and the pGEM-T-Pig β casein 5'+3' vector was digested with BamHI and NotI to prepare a 10.3-kb insert. The resulting two restriction fragments were ligated to construct a pBC1-Pig β casein cloning vector.

Figure 2:
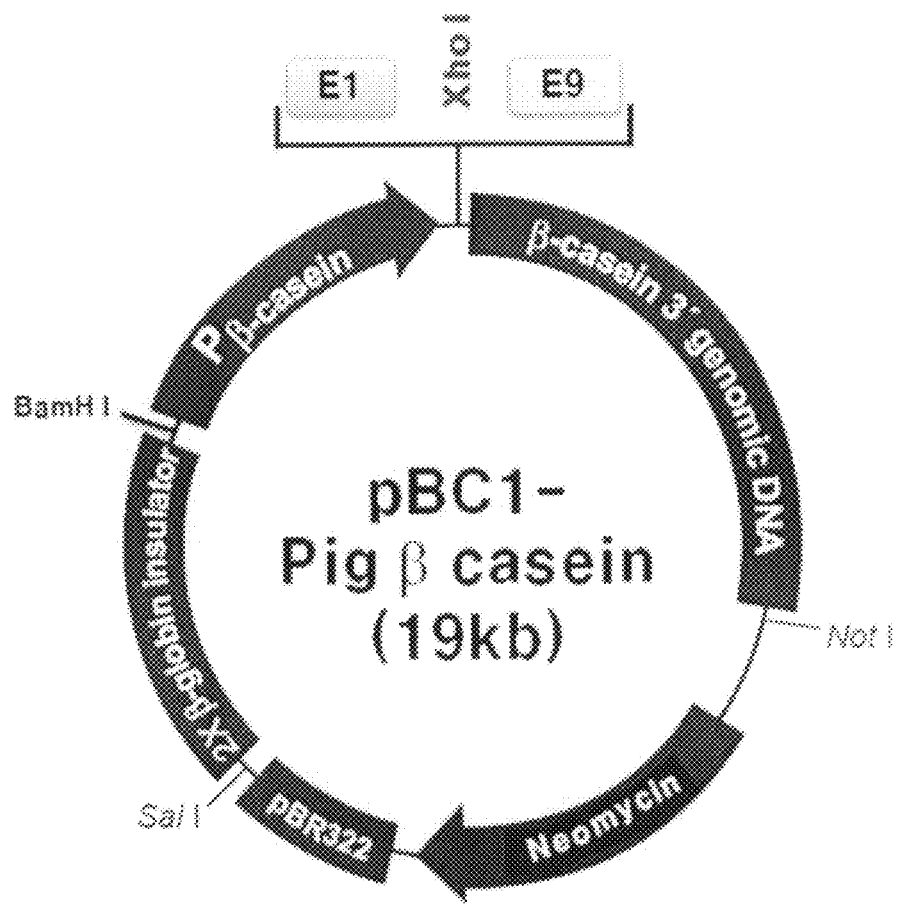
FIG. 2 shows a structure of a pBC1-Pig β casein expression vector in accordance with the present invention.

The structure of the constructed pBC1-Pig β casein cloning vector is shown in FIG. 2.

In FIG. 2, $P_{β-casein}$ represents a promoter sequence (SEQ ID NO: 2) containing an exon 1 (E1). The exon 1 refers to an exon which is first arranged in the direction of in the sequence of SEQ ID NO: 1.

In FIG. 2, β-casein 3' genomic DNA represents a 3' arm sequence (SEQ ID NO: 5) containing an exon 9 (E9). The exon 9 refers to the $9^{th}$ exon in the direction of 5'→3' in the sequence of SEQ ID NO: 1.

Due to having an XhoI restriction site, the gene of a target protein can be inserted into the vector.

2×3-globin insulator and pBR322 respectively represent an insulator and a vector component derived from the pBC1 vector. Neomycin represents a neomycin-resistant gene which is derived from the pEGFP-N1 vector (Clontech, USA).

The thus-constructed pBC1-Pig β casein vector was deposited with the Korean Collection for Type Cultures (KCTC), the Korean Research Institute of Bioscience and Biotechnology (KRIBB, Daejon, Korea), under Accession Number KCTC 11327BP.

Example 3

Construction of pBC1-Pig β Casein+hEPO-WPRE Vector

Erythropoietin (hEPO) was cloned into a vector having substitution of an ampicillin-resistant gene of a pBC1 vector (Invitrogen, USA) with a neomycin-resistant gene {A 'neo' gene capable of conferring drug resistance to G418 was obtained from a pEGFP-N1 vector (Clontech, USA) by amplification of a 1.9-kb PCR product (SEQ ID NO: 45) using a forward primer 5'-GCGGCCGCGCGCGTCAG-GTGGCAC-3' (SEQ ID NO: 43) and a reverse primer 5'-CGATCGGACGCTCAGTGGAACGAAAACTC-3' (SEQ ID NO: 44), and was then cloned into a pGEM T-easy vector. The 1.9-kb neo gene cloned into the T-vector was digested with restriction endonucleases NotI and PvuI to prepare an insert. In addition, an amp gene (ampicillin-resistance gene) region of the pBC1 vector was removed by NotI and PvuI cleavage to prepare a vector. The resulting insert fragment and vector part were ligated to construct a pBC1 vector into which the neo gene (neomycin-resistance gene) was inserted}, followed by replacement of the goat beta-casein promoter region and the 3' genomic DNA region present in the vector with a promoter sequence (SEQ ID NO: 3) and a 3' arm sequence (SEQ ID NO: 5). In addition, expression of hEPO was maximized by adding to a 3' side of hEPO, WPRE (woodchuck hepatitis virus post-transcriptional regulatory element) which is known to augment protein expression through stabilization of mRNA.

hEPO and WPRE were each subjected to PCR amplification (PT-200, BIO-RAD). PCR was carried out as follows: one cycle of denaturation at 94° C. for 5 minutes; and 35 cycles of denaturation at 94° C. for 30 seconds, primer annealing at 56° C. for 30 seconds, and elongation at 72° C. for 2.5 minutes for hEPO and 30 seconds for WPRE. Each of the resulting PCR products 2.3 kb (SEQ ID NO: 60) and 0.6 kb (SEQ ID NO: 61) was cloned into a pGEM-T vector (Promega, USA), followed by confirmation of the sequence thereof. The pGEM-T vector harboring hEPO was digested with EcoRV and NotI, and the pGEM-T vector harboring WPRE was digested with EcoRV and NotI. The resulting two restriction fragments were ligated.

Primer sequences used for PCR amplification of hEPO and WPRE are as follows.

TABLE 8

| Primers | | SEQ ID NO |
|---|---|---|
| Forward primer for hEPO amplification | 5'-GGATCCTGTGGTCACCCGGCGCGC-3' | 56 |
| Reverse primer for hEPO amplification | 5'-GATATCCCATGGGACAGGCTGGCGCT-3' | 57 |
| Forward primer for WPRE amplification | 5'-GATATCTCTGTTCCTGTTAATCAACCTC-3' | 58 |
| Reverse primer for WPRE amplification | 5'-GCGGCCGCGAGCCCGAGGCGAAACAG-3' | 59 |

The pBC1 vector was digested with BamHI and NotI to remove the goat beta-casein promoter and the 3' genomic DAN region, thereby preparing a vector. In addition, hEPO+WPRE cloned into the pGEM-T vector was digested with BamHI and NotI to prepare a 2.9-kb insert. The resulting vector and insert were ligated to construct pBC1+hEPO-WPRE. For cloning of the promoter and the 3' arm region into pBC1+hEPO-WPRE, the promoter sequence 5.3 kb (SEQ ID NO: 3) and the 3' arm sequence 5.0 kb (SEQ ID NO: 5) were cloned into a pGEM-T vector (Promega, USA) by means of PCR amplification.

Primer sequences used for PCR amplification of the promoter sequence and the 3' arm sequence are as follows.

TABLE 9

| Primers | | SEQ ID NO |
|---|---|---|
| Forward primer for promoter amplification | 5'-GGATCCGCTATGCAATCTCATGGAAAG-3' | 62 |
| Reverse primer for promoter amplification | 5'-GGATCCTGACCAGGGTCAACATCTACT-3' | 63 |
| Forward primer for 3' arm amplification | 5'-GCGGCCGCCTGCACTTCATTCTCCTGGATAA-3' | 64 |
| Reverse primer for 3' arm amplification | 5'-GCGGCCGCTTACAGTAAGACCTTCAGGAGCA-3' | 65 |

Analogously the procedure of Example 2, point mutations were introduced into two BamHI sites (GGATCC) present on the porcine beta-casein promoter sequence, by a Site-Directed Mutagenesis kit (iNtRON) using primers (SEQ ID NO: 50 to SEQ ID NO: 53). The pBC1+hEPO-WPRE vector was digested with BamHI, and treated with alkaline phosphatase (CIP) for 30 minutes to prepare a vector. In addition, the pGEM-T vector containing the point-mutated porcine beta-casein 5' promoter DNA was digested with BamHI to prepare a 5.4-kb insert (SEQ ID NO: 3). The resulting two restriction fragments were ligated to clone a pBC1-porcine beta-casein 5'+EPO-WPRE vector. The pBC1-porcine beta-casein 5'+hEPO-WPRE vector was digested with NotI and treated with CIP for 30 minutes to prepare a vector. In addition, the pGEM-T vector containing the porcine beta-casein 3' arm DNA was digested with NotI to prepare a 5.0-kb insert (SEQ ID NO: 5). The resulting two restriction fragments were ligated to construct a pBC1-Pig β casein+hEPO-WPRE vector.

Figure 3:
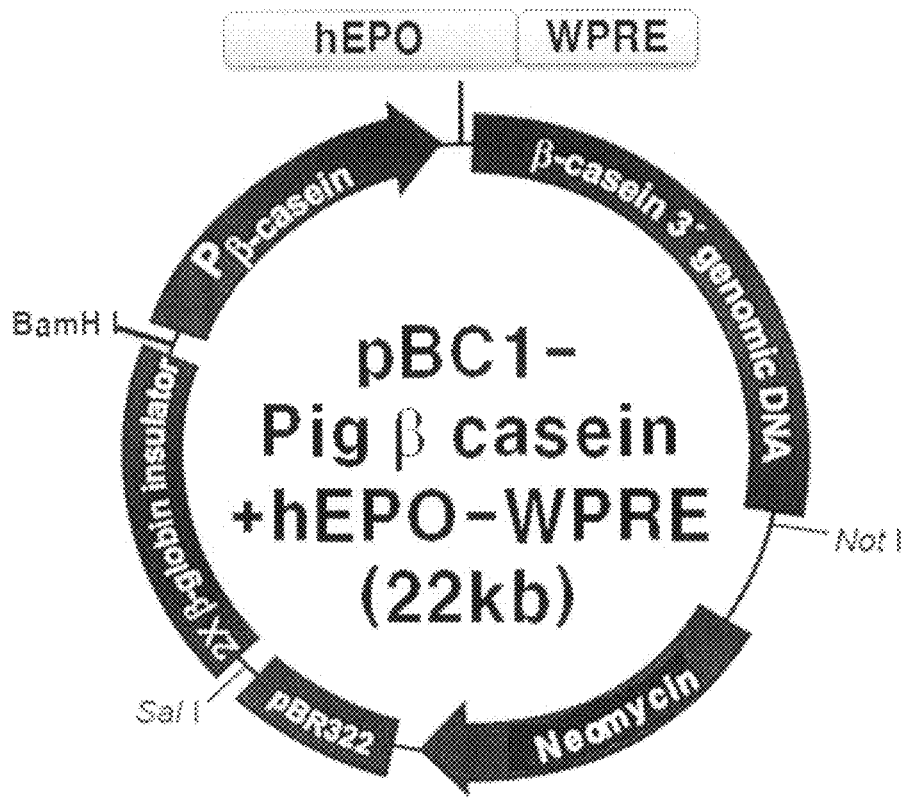
FIG. 3 shows a structure of a pBC1-Pig β casein+hEPO-WPRE expression vector in accordance with the present invention.

The structure of the constructed pBC1-Pig β casein+hEPO-WPRE vector is shown in FIG. 3.

In FIG. 3, $P_{\beta\text{-}casein}$ represents a porcine beta-casein promoter sequence (SEQ ID NO: 3), and β-casein 3' genomic DNA represents a 3' arm sequence (SEQ ID NO: 5).

hEPO represents a human EPO gene, and WPRE represents a woodchuck hepatitis virus post-transcriptional regulatory element gene.

2×β-globin insulator and pBR322 respectively represent an insulator and a vector component derived from the pBC1 vector. Neomycin represents a neomycin-resistant gene which is derived from the pEGFP-N1 vector (Clontech, USA).

The thus-constructed pBC1-Pig β casein+hEPO-WPRE vector was deposited with the Korean Collection for Type Cultures (KCTC), the Korean Research Institute of Bioscience and Biotechnology (KRIBB, Daejon, Korea), under Accession Number KCTC 11328BP.

Example 4

Construction of Pig βCasein–hEPO Knock-in Vector Using Porcine Beta-Casein Gene

1) Cloning of pGEM-T-hEPO Vector

For construction of a porcine beta-casein hEPO knock-in vector capable of confirming correct introduction of a gene into a specific site by TK gene selection, two pairs of specific primers (SEQ ID NO: 66 to 68) were prepared which contain from the beginning of an exon 2 region to an initiation codon in the porcine beta-casein gene and enables amplification of a sequence of the hEPO gene from after the initiation codon. With the above-prepared primer containing the exon 2 region of porcine beta-casein, primary PCR amplification (PT-200, BIO-RAD) was carried out from the human genomic DNA. PCR was carried out as follows: one cycle of denaturation at 94° C. for 5 minutes; and 30 cycles of denaturation at 94° C. for 30 seconds, primer annealing at 56° C. for 30 seconds and elongation at 72° C. for 2.5 minutes. Secondary PCR amplification (PT-200, BIO-RAD) was then carried out using the resulting primary PCR products as templates. PCR was carried out as follows: one cycle of denaturation at 94° C. for 5 minutes; and 30 cycles of denaturation at 94° C. for 30 seconds, primer annealing at 56° C. for 30 seconds and elongation at 72° C. for 2.5 minutes.

The PCR-amplification product 2.3-kb hEPO gene (SEQ ID NO: 60) containing the sequence spanning from the porcine beta-casein exon 2 region to the initiation codon was cloned into a pGEM-T vector (Promega, USA) to construct a vector (pGEM-T-hEPO).

Primer sequences used for PCR amplification of hEPO are as follows.

TABLE 10

| Primers | | SEQ ID NO |
|---|---|---|
| First forward primer for hEPO amplification | 5'-GACTTGATCGCCATGGGGGTGC ACGGTGAGTACTC-3' | 66 |
| Second forward primer for hEPO amplification | 5'-GATATCATTCACAGGACTTGAT CGCCATGGGGG-3' | 67 |
| Reverse primer for hEPO amplification | 5'-GAATTCATGGGACAGGCTGGCG CTGA-3' | 68 |

2) Construction of pGEM-T-Pig βcasein 5' arm and pGEM-T-Pig βcasein 3' arm

In order to clone the promoter sequence (5' arm) and 3' arm sequence (3' arm) of the porcine beta-casein gene, primers of SEQ ID NO: 69 to SEQ ID NO: 72 were constructed and PCR amplification was then carried out from the porcine genomic DNA. The resulting PCR products 4.9 kb (SEQ ID NO: 4) and 5.0 kb (SEQ ID NO: 5) were cloned into a pGEM-T vector to thereby construct pGEM-T-Pig βcasein 5' arm and pGEM-T-Pig βcasein 3' arm.

TABLE 11

| Primers | | SEQ ID NO |
|---|---|---|
| Forward primer for promoter amplification | 5'-GTCGACAGTTGTAGCTGCTGAC CTACAC-3' | 69 |
| Reverse primer for promoter amplification | 5'-GATATCGGGGAAATGAGGGAAA AAATGTAT-3' | 70 |
| Forward primer for 3' arm amplification | 5'-GCGGCCGCCTGCACTTCATTCT CCTGGATAA-3' | 71 |
| Reverse primer for 3' arm amplification | 5'-CCGCGGTTACAGTAAGACCTTC AGGAGCA-3' | 72 |

3) Construction of Lox A Neo-hEPO Vector

A Lox A neo vector (Gerard Karsenty's, Department of Genetics and Development, College of Physicians and Surgeons, Columbia University, New York, N.Y. 10032) was restricted with EcoRV and EcoRI to prepare a vector. In addition, the cloned pGEM-T-hEPO was restricted with EcoRV and EcoRI to prepare a 2.3-kb insert (SEQ ID NO: 60). The resulting two restriction fragments were ligated to construct a Lox A neo-hEPO vector.

4) Construction of Lox A Neo-hEPO-Poly(A) Vector

In order to insert a poly(A) sequence for stabilization of RNA into a 3' side of the Lox A neo-hEPO vector, the Lox A neo-hEPO vector was restricted with EcoRI and treated with alkaline phosphatase for 30 minutes to prepare a vector. In addition, the bovine growth hormone (BGH) poly(A) derived from a pcDNA3 vector (Invitrogen, USA) was restricted with EcoRI to prepare a 0.3-kb insert. The resulting two restriction fragments were ligated to construct a Lox A neo-hEPO-poly (A) vector.

5) Construction of Lox A Neo-hEPO-Poly(A)-5' Arm Vector

In order to insert a Pig β casein 5' arm into a 5'side of the Lox A neo-hEPO-poly(A) vector, the Lox A neo-hEPO-poly (A) vector was restricted with SalI and EcoRV to prepare a vector. In addition, the cloned pGEM-T-Pig β casein 5' arm vector was restricted with SalI and EcoRV to prepare a 4.9-kb insert (SEQ ID NO: 4). The resulting two restriction fragments were ligated to construct a Lox A neo-hEPO-poly(A)-5' arm vector.

6) Construction of Lox A Neo-hEPO-Poly(A)-5' Arm-3' Arm Vector

In order to insert a Pig β casein 3' arm into a 3' side of the Lox A neo-hEPO-poly(A)-5' arm vector, the Lox A neo-hEPO-poly(A)-5' arm vector was restricted with NotI and treated with alkaline phosphatase for 30 minutes to construct a vector. The cloned pGEM-T-Pig β casein 3' arm vector was restricted with NotI to prepare a 5.0-kb insert (SEQ ID NO: 5). The resulting two restriction fragments were ligated to construct a Lox A neo-hEPO-poly(A)-5' arm-3' arm vector.

7) Construction of Lox A Neo-hEPO-Poly(A)-5' Arm-3' Arm-TK Vector

In order to insert a Herpes simplex virus-thymidine kinase (HSV-tk) gene as an apoptotic gene into a 3' side of the Lox A neo-hEPO-poly(A)-5' arm-3' arm vector, the Lox A neo-hEPO-poly(A)-5' arm-3' arm vector was restricted with SacII and treated with alkaline phosphatase for 30 minutes to prepare a vector. A pBS-TK vector (Gerard Karsenty's, Department of Genetics and Development, College of Physicians and Surgeons, Columbia University, New York, N.Y. 10032) was restricted with NotI to prepare a 2.3-kb insert (encoding the Herpes simplex virus-thymidine kinase gene). The resulting two restriction fragments were ligated to construct a Lox A neo-hEPO-poly(A)-5' arm-3' arm-TK vector (Pig β casein–hEPO knock-in vector).

Figure 4:
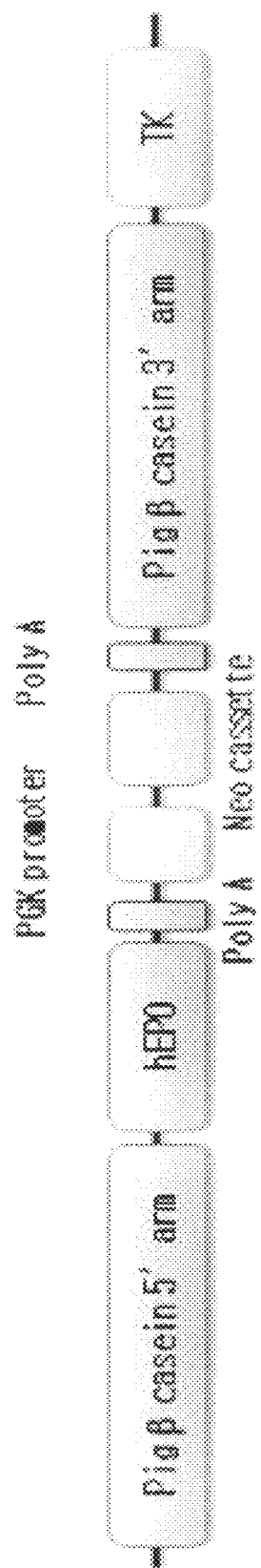
FIG. 4 shows a structure of a Pig β casein–hEPO knock-in vector in accordance with the present invention.

The structure of the constructed Pig β casein–hEPO knock-in vector is shown in FIG. 4.

In FIG. 4, Pig β casein 5' arm represents the porcine beta casein promoter (SEQ ID NO: 4), and Pig β casein 3' arm represents the 3' arm (SEQ ID NO: 5).

hEPO represents a human EPO gene, poly(A) represents a poly(A) signal-encoding gene, Neo cassette represents a neomycin-resistant gene which serves as a positive selective gene, PGK promoter represents a phosphoglycerate kinase (PGK) promoter, and TK represents a Herpes simplex virus-thymidine kinase (HSV-tk) gene which serves as a negative selective gene and is derived from the pBS-TK vector.

The thus-constructed Pig β casein–hEPO knock-in vector was deposited with the Korean Collection for Type Cultures (KCTC), the Korean Research Institute of Bioscience and Biotechnology (KRIBB, Daejon, Korea), under Accession Number KCTC 11329BP.

INDUSTRIAL APPLICABILITY

As apparent from the above description, a porcine beta-casein gene of the present invention, a promoter thereof, and an expression vector and transgenic animal using the same allow for high-concentration secretion of target proteins in milk, which consequently will provide benefits for the production of useful proteins that are medically and pharmaceutically valuable.

[Deposit certification of microorganisms]

BUDAPEST TREATY ON THE INTERNATIONAL RECOGNITION OF THE DEPOSIT
OF MICROORGANISMS FOR THE PURPOSE OF PATENT PROCEDURE

INTERNATIONAL FORM

RECEIPT IN THE CASE OF AN ORIGINAL DEPOSIT issued pursuant to Rule 7.1

TO : CHO, Seong-Hwan
CHO-A PHARM Co., Ltd.
ACE Techno-Tower 1F, 55-7 Mullae-dong 3ga, Youngdungpo-gu, Seoul 150-835
Republic of Korea

| I. IDENTIFICATION OF THE MICROORGANISM | |
|---|---|
| Identification reference given by the DEPOSITOR:<br><br>*Escherichia coli*<br>DH10B/pBC1-pig β casein | Accession number given by the INTERNATIONAL DEPOSITARY AUTHORITY:<br><br>KCTC 11327BP |

| II. SCIENTIFIC DESCRIPTION AND/OR PROPOSED TAXONOMIC DESIGNATION |
|---|
| The microorganism identified under I above was accompanied by:<br>[ x ] a scientific description<br>[ ] a proposed taxonomic designation<br>(Mark with a cross where applicable) |

| III. RECEIPT AND ACCEPTANCE |
|---|
| This International Depositary Authority accepts the microorganism identified under I above, which was received by it on April 29, 2008. |

| IV. RECEIPT OF REQUEST FOR CONVERSION |
|---|
| The microorganism identified under I above was received by this International Depositary Authority on  and a request to convert the original deposit to a deposit under the Budapest Treaty was received by it on |

| V. INTERNATIONAL DEPOSITARY AUTHORITY | |
|---|---|
| Name: Korean Collection for Type Cultures<br><br>Address: Korea Research Institute of Bioscience and Biotechnology (KRIBB)<br>111 Gwahangno, Yuseong-gu,<br>Daejeon 305-806<br>Republic of Korea | Signature(s) of person(s) having the power to represent the International Depositary Authority of authorized official(s):<br><br>OH, Hee-Mock, Director<br>Date: May 8, 2008 |

Form BP/4 (KCTC Form 17)    sole page

BUDAPEST TREATY ON THE INTERNATIONAL RECOGNITION OF THE DEPOSIT
OF MICROORGANISMS FOR THE PURPOSE OF PATENT PROCEDURE

INTERNATIONAL FORM

RECEIPT IN THE CASE OF AN ORIGINAL DEPOSIT issued pursuant to Rule 7.1

TO : CHO, Seong-Hwan
CHO-A PHARM Co., Ltd.
ACE Techno-Tower 1F, 55-7 Mullae-dong 3ga, Youngdungpo-gu, Seoul 150-835
Republic of Korea

| I. IDENTIFICATION OF THE MICROORGANISM | |
|---|---|
| Identification reference given by the DEPOSITOR: *Escherichia coli* DH10B/pBC1-pig β casein+hEPO-WPRE | Accession number given by the INTERNATIONAL DEPOSITARY AUTHORITY: KCTC 11328BP |

| II. SCIENTIFIC DESCRIPTION AND/OR PROPOSED TAXONOMIC DESIGNATION |
|---|
| The microorganism identified under I above was accompanied by:<br>[ x ] a scientific description<br>[ ] a proposed taxonomic designation<br>(Mark with a cross where applicable) |

| III. RECEIPT AND ACCEPTANCE |
|---|
| This International Depositary Authority accepts the microorganism identified under I above, which was received by it on April 29, 2008. |

| IV. RECEIPT OF REQUEST FOR CONVERSION |
|---|
| The microorganism identified under I above was received by this International Depositary Authority on                   and a request to convert the original deposit to a deposit under the Budapest Treaty was received by it on |

| V. INTERNATIONAL DEPOSITARY AUTHORITY | |
|---|---|
| Name: Korean Collection for Type Cultures | Signature(s) of person(s) having the power to represent the International Depositary Authority of authorized official(s): |
| Address: Korea Research Institute of Bioscience and Biotechnology (KRIBB) 111 Gwahangno, Yuseong-gu, Daejeon 305-806 Republic of Korea | OH, Hee-Mock, Director<br>Date: May 8, 2008 |

Form BP/4 (KCTC Form 17)  sole page

BUDAPEST TREATY ON THE INTERNATIONAL RECOGNITION OF THE DEPOSIT
OF MICROORGANISMS FOR THE PURPOSE OF PATENT PROCEDURE

INTERNATIONAL FORM

RECEIPT IN THE CASE OF AN ORIGINAL DEPOSIT issued pursuant to Rule 7.1

TO : CHO, Seong-Hwan
CHO-A PHARM Co., Ltd.
ACE Techno-Tower 1F, 55-7 Mullae-dong 3ga, Youngdungpo-gu, Seoul 150-835
Republic of Korea

| I. IDENTIFICATION OF THE MICROORGANISM | |
|---|---|
| Identification reference given by the DEPOSITOR: <br><br> *Escherichia coli* <br> DH10B/Pig β-casein-hEPO knock-in | Accession number given by the INTERNATIONAL DEPOSITARY AUTHORITY: <br><br> KCTC 11329BP |
| II. SCIENTIFIC DESCRIPTION AND/OR PROPOSED TAXONOMIC DESIGNATION : | |
| The microorganism identified under I above was accompanied by: <br> [ x ] a scientific description <br> [ ] a proposed taxonomic designation <br> (Mark with a cross where applicable) | |
| III. RECEIPT AND ACCEPTANCE | |
| This International Depositary Authority accepts the microorganism identified under I above, which was received by it on April 29, 2008. | |
| IV. RECEIPT OF REQUEST FOR CONVERSION | |
| The microorganism identified under I above was received by this International Depositary Authority on             and a request to convert the original deposit to a deposit under the Budapest Treaty was received by it on | |
| V. INTERNATIONAL DEPOSITARY AUTHORITY | |
| Name: Korean Collection for Type Cultures <br><br> Address: Korea Research Institute of Bioscience and Biotechnology (KRIBB) <br> 111 Gwahangno, Yuseong-gu, <br> Daejeon 305-806 <br> Republic of Korea | Signature(s) of person(s) having the power to represent the International Depositary Authority of authorized official(s): <br><br> OH, Hee-Mock, Director <br> Date: May 8, 2008 |

Form BP/4 (KCTC Form 17)                                       sole page

What is claimed is:

1. An expression vector, comprising one or more nucleotide sequences selected from the group consisting of SEQ ID No. 2, SEQ ID No. 3, and SEQ ID No. 4, wherein the vector further comprises the nucleotide sequence as set forth in SEQ ID No. 5.

2. The expression vector of claim 1 wherein the vector further comprises one or more elements selected from a selective marker, an insulator, and a woodchuck hepatitis virus posttranscriptional regulatory element (WPRE).

3. The expression vector of claim 2, wherein the vector has a cleavage map as shown in FIG. 2.

4. The expression vector of claim 3, wherein the vector is pBC1-Pig β-casein.

5. The expression vector of claim 1 or claim 2, further comprising a target protein-encoding sequence at a 3' side of the promoter sequence.

6. The expression vector of claim 5, wherein the target protein is human erythropoietin (hEPO).

7. The expression vector of claim 6, wherein the vector has a cleavage map as shown in FIG. 3.

8. The expression vector of claim 7, wherein the vector is pBC1-Pig-βcasein+hEPO-WPRE.

9. The expression vector of claim 1, wherein the vector is a knock-in vector.

10. The expression vector of claim 9, wherein the knock-in vector further comprises a selective marker.

11. The expression vector of claim 10, wherein the knock-in vector has a cleavage map as shown in FIG. 4.

12. The expression vector of claim 11, wherein the knock-in vector is Pig-β-casein–hEPO.

13. A isolated non-human animal somatic cell, comprising the expression vector of claim 1.

* * * * *

UNITED STATES PATENT AND TRADEMARK OFFICE
CERTIFICATE OF CORRECTION

| | |
|---|---|
| PATENT NO. | : 8,420,388 B2 |
| APPLICATION NO. | : 12/737318 |
| DATED | : April 16, 2013 |
| INVENTOR(S) | : Kim et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 32 days.

Signed and Sealed this
Fifth Day of November, 2013

Teresa Stanek Rea
*Deputy Director of the United States Patent and Trademark Office*

UNITED STATES PATENT AND TRADEMARK OFFICE
CERTIFICATE OF CORRECTION

Page 1 of 1

PATENT NO. : 8,420,388 B2
APPLICATION NO. : 12/737318
DATED : April 16, 2013
INVENTOR(S) : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 33 days.

This certificate supersedes the Certificate of Correction issued November 5, 2013.

Signed and Sealed this
Third Day of December, 2013

Margaret A. Focarino
*Commissioner for Patents of the United States Patent and Trademark Office*